United States Patent [19]
Adams et al.

[11] Patent Number: 6,060,288
[45] Date of Patent: *May 9, 2000

[54] METHOD FOR PERFORMING AMPLIFICATION OF NUCLEIC ACID ON SUPPORTS

[75] Inventors: Christopher P. Adams, Winter Hill; Truett C. Boles, Waltham; Andrew R. Muir, Cohasset, all of Mass.; Stephen J. Kron, Oak Park, Ill.

[73] Assignee: Mosaic Technologies, Boston, Mass.

[*] Notice: This patent is subject to a terminal disclaimer.

[21] Appl. No.: 08/800,840

[22] Filed: Feb. 14, 1997

Related U.S. Application Data

[63] Continuation-in-part of application No. 08/776,859, filed as application No. PCT/US95/09905, Aug. 3, 1995, which is a continuation-in-part of application No. 08/285,385, Aug. 3, 1994, Pat. No. 5,641,658.

[51] Int. Cl.[7] .............................. C12P 19/34; C12Q 1/68; C07H 21/04

[52] U.S. Cl. .................................. 435/91.2; 435/5; 435/6; 435/91.1; 435/91.21; 536/24.3; 536/24.31; 536/24.32; 536/24.33

[58] Field of Search .......................... 435/5, 6, 7.1, 91.1, 435/91.2, 91.21; 536/24.3, 24.31, 24.32, 34.33; 530/387.1, 388.1; 436/518, 501

[56] References Cited

U.S. PATENT DOCUMENTS

| | | | |
|---|---|---|---|
| 5,302,509 | 4/1994 | Cheeseman | 435/6 |
| 5,474,796 | 12/1995 | Brennan | 427/2.13 |
| 5,641,568 | 6/1997 | Adams et al. | 435/91.2 |
| 5,645,801 | 7/1997 | Bouma et al. | 422/68.1 |
| 5,683,872 | 11/1997 | Rudert et al. | 436/6 |
| 5,690,894 | 11/1997 | Pinkel et al. | 422/68.1 |

FOREIGN PATENT DOCUMENTS

| | | |
|---|---|---|
| 0 374 665 A3 | 6/1990 | European Pat. Off. . |
| 0 487 104 A1 | 5/1992 | European Pat. Off. . |
| 0 701 001 A2 | 3/1996 | European Pat. Off. . |
| 2 233 654 | 1/1991 | United Kingdom . |
| 90/02205 | 3/1990 | WIPO . |
| 90/06042 | 6/1990 | WIPO . |
| 90/09455 | 8/1990 | WIPO . |
| 92/04469 | 3/1992 | WIPO . |
| 93/04199 | 3/1993 | WIPO . |
| 93/09250 | 5/1993 | WIPO . |
| 94/05414 | 3/1994 | WIPO . |
| 94/24312 | 10/1994 | WIPO . |
| WO 95/12416 | 10/1995 | WIPO . |
| 96/04404 | 2/1996 | WIPO . |
| WO 96/24688 | 8/1996 | WIPO . |
| WO 97/41256 | 11/1997 | WIPO . |
| WO 97/45554 | 12/1997 | WIPO . |

OTHER PUBLICATIONS

Abel, A.P., et al., "Fiber–Optic Evanescent Wave Biosensor for the Detection of Oligonucleotides," *Anal. Chem.*, 68:2905–2912 (1996).

Piunno, P.A.E., and Krull, U.J., "Fiber–Optic DNA Sensor for Fluorometric Nucleic Acid Determination," *Anal. Chem.*, 67:2635–2643 (1995).

Kulp, T.J. et al., "Polymer Immobilized Enzyme Optrodes for the Detection of Penicillin," *Anal. Chem.*, 59:2849–2853 (1987).

Bronk, K.S., et al., "Combined Imaging and Chemical Sensing Using a Single Optical Imaging Fiber," *Anal. Chem.*, 67:2750–2757 (1995).

Eggleston, A.K., et al., "A Helicase Assay Based on the Displacement of Fluorescent, Nucleic Acid–Binding Ligands," *Nucleic Acids Res.*, 24(7):1179–1186 (1996).

Higuchi, R., et al., "Kinetic PCR Analysis: Real–Time Monitoring of DNA Amplification Reactions," *Bio/Technology*, 11:1026–1030 (1993).

Manley, J.L., et al., "DNA–Dependent Transcription of Adenovirus Genes in a Soluble Whole–Cell Extract," *Proc. Natl. Acad. Sci. USA*, 77(7):3855–3859 (1980).

VanNess, J., et al., "A Versatile Solid Support System for Oligodeoxynucleotide Probe–Based Hybridization Assays," *Nucleic Acids Res.*, 19(12):3345–3350 (1991).

Maskos, U. and Southern, E.M., "Parallel Analysis of Oligodeoxyribonucleotide (Oligonucleotide) Interactions. 1. Analysis of Factors Influencing Oligonucleotide Duplex Formation," *Nulc. Acids Res.*, 1 (7):1675–1678 (1992).

Ferguson, J., et al., "A Fiber–Optic DNA Biosensor Microarray for the Analysis of Gene Expression," *Nature Biotechnology*, 14:1681–1684 (1996).

Monkholm, C., et al., "Polymer Modification of Fiber Optic Chemical Sensors as a Method of Enhancing Fluorescence Signal for pH Measurement," *Anal. Chem.*, 58:1427–1430 (1986).

Babic et al, "MutS interaction with mismatch and alkylated base containing DNA molecules detected by optical biosensor", Mutation research 372:87–96, Nov. 1996.

Winn–Deen et al, "Non–radioactive detection of mycobacterium tuberculosis LCR products in a microtiter plate format", Mol. Cell. Probes 7:179–186, 1993.

Stratagene catalog, p. 39, 1988.

*Primary Examiner*—Jeffrey Fredman
*Attorney, Agent, or Firm*—Hamilton, Brook, Smith & Reynolds, P.C.

[57] ABSTRACT

This invention features methods, apparatus and kits for performing nucleic acid hybridization and amplification reactions on a support. Such methods and apparatus are useful in diagnostic and therapeutic processes for synthesizing nucleic acid and detecting target nucleic acids in a sample.

58 Claims, 22 Drawing Sheets

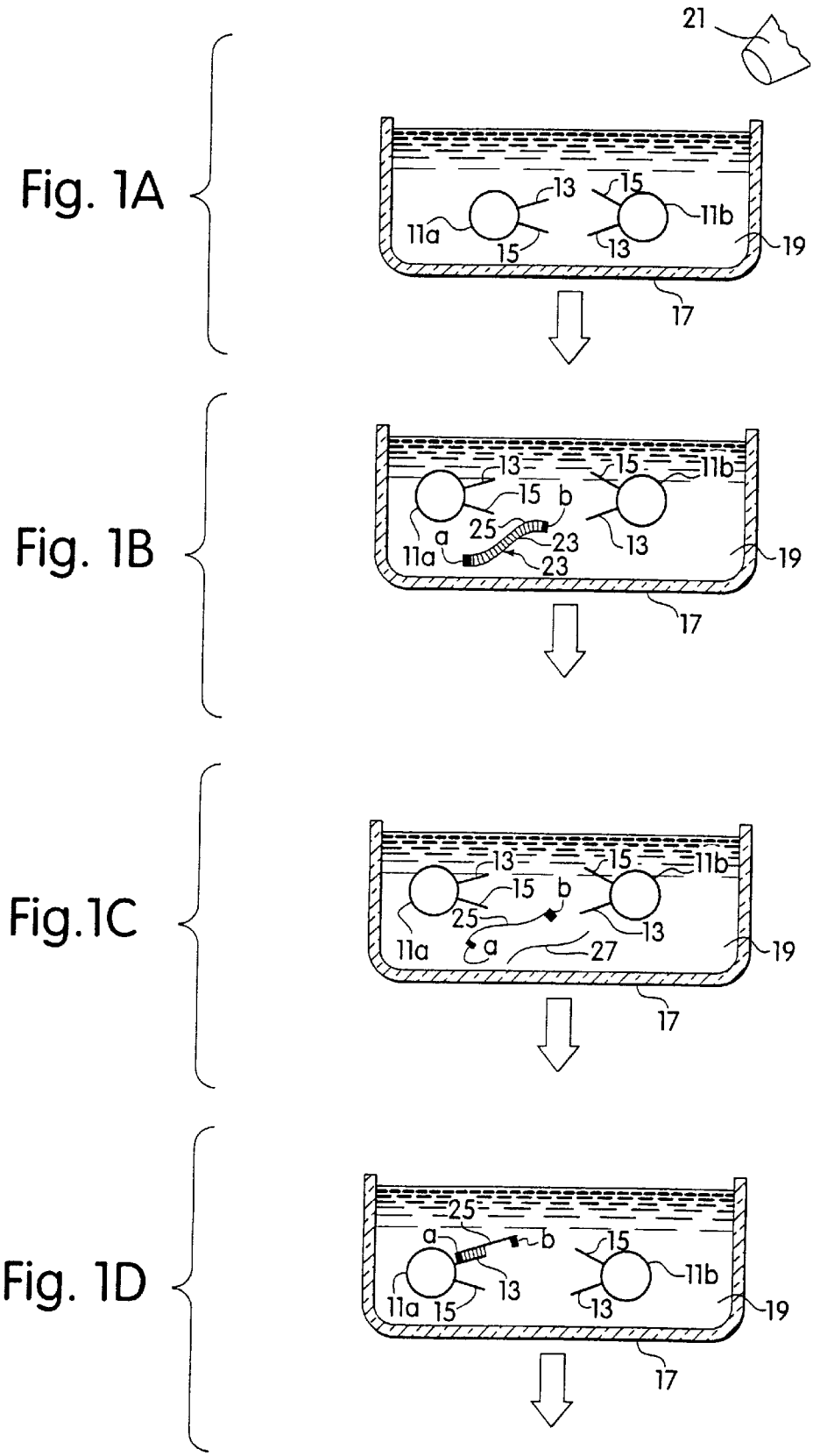

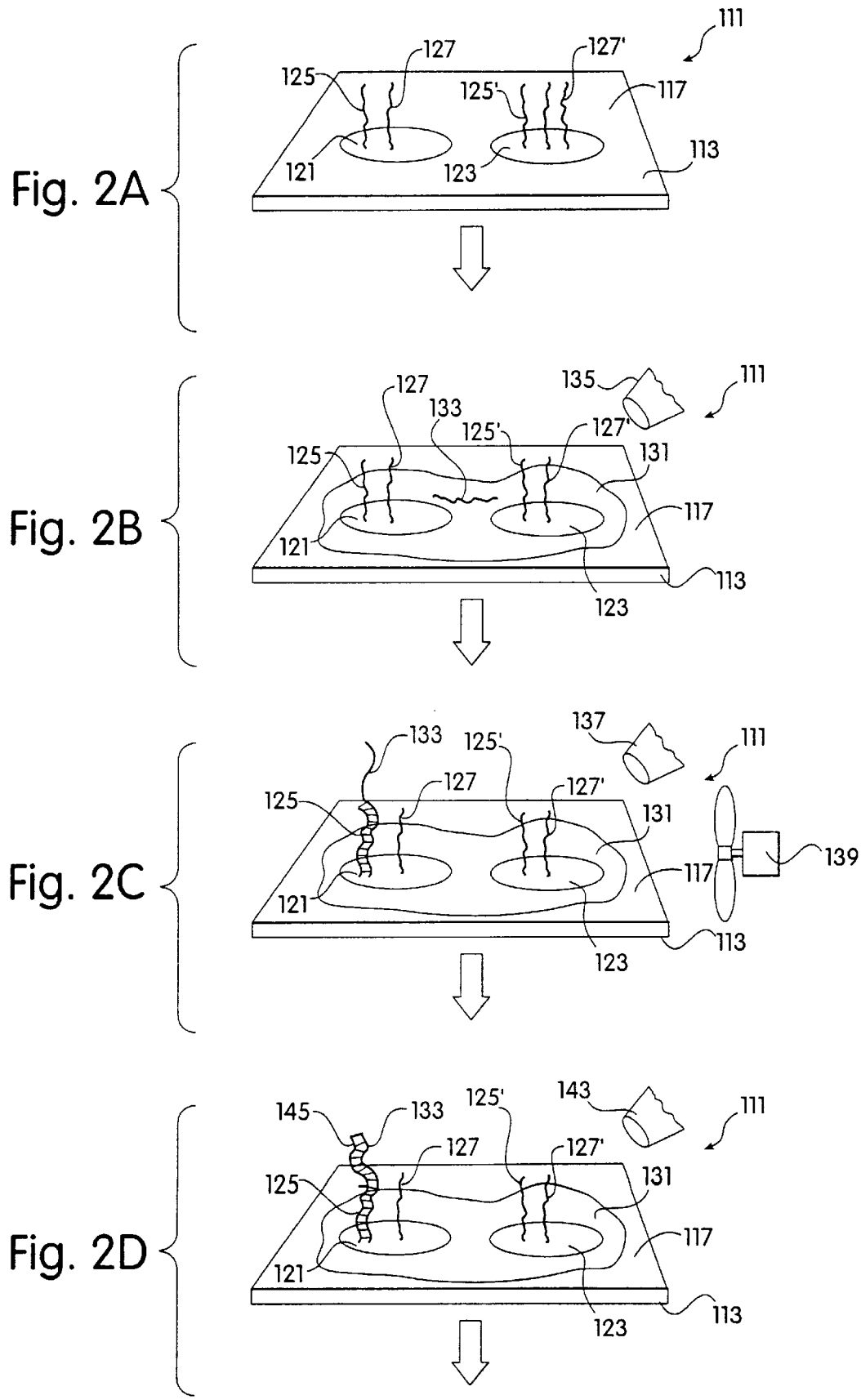

METHOD FOR PERFORMING AMPLIFICATION OF NUCLEIC ACID ON SUPPORTS

RELATED APPLICATIONS

This application is a continuation-in-part of prior Ser. No. 08/776,859 filed Feb. 3, 1997, which is the U.S. National Phase of PCT/US95/09905 filed Aug. 3, 1995, which is a continuation-in-part of prior Ser. No. 08/285,385 filed Aug. 3, 1994, now U.S. Pat. No. 5,641,658, issued on Jun. 24, 1997 the teachings of which are hereby incorporated herein by reference in their entirety.

BACKGROUND OF THE INVENTION

Molecular diagnosis of genetic defects and diseases requires techniques that are capable of detecting minute quantities of DNA and RNA in a sample, or techniques that are extremely sensitive to detect mutations in DNA. For example, techniques such as southern blot, polymerase chain reaction, reverse transcriptase-polymerase chain reaction and ligase chain reaction have been extensively used to detect microbial and viral pathogens, such as HIV, and to diagnosis cancers and genetic diseases, such as cystic fibrosis and muscular dystrophy. Specifically, techniques such as polymerase chain reaction, or PCR, amplify small quantities of the target nucleotide sequence to obtain detectable quantities.

However, techniques such as PCR typically require additional separation procedures prior to detection of the target sequence to achieve adequate sensitivity. Moreover, PCR has a high rate of sample-to-sample contamination which decreases the accuracy of the procedure.

The development of simple, fast and reliable amplification-based assays to detect target nucleic acids will greatly aid molecular diagnosis.

SUMMARY OF THE INVENTION

The present invention is based on the demonstration that amplification and optical detection of target nucleic acid sequences can be achieved on a solid support, which greatly facilitates detection of the target sequence in a rapid and reproducible manner. The methods, apparatus and kits described herein can be used to detect minute quantities of a target nucleic acid sequence in a wide variety of test samples, and are particularly useful to assess levels of DNA repair following exposure to agents which induce lesions in DNA.

In one embodiment of the present invention, a method is provided for the detection of the presence of (or the absence of) a target nucleic acid sequence in a test sample using a solid support and an amplification reaction, such as polymerase chain reaction, or ligase chain reaction. In the method, a test sample to be assessed for the presence or absence of a target nucleic acid sequence is provided.

Also provided is a solid support, such as an optical fiber. Other suitable solid supports are described herein. The optical fiber has a proximal end and a distal end. On the distal end of the optical fiber, an oligonucleotide (also referred to herein as a polynucleotide) is attached to the support. Attachment of the oligonucleotide to the support can be accomplished in a number of ways, as described herein, and as well known to those of skill in the art. Typically, attachment is accomplished via an intermediate, or chemical reagent. Such attachment of the oligonucleotide to the support immobilizes the oligonucleotide on the support. In one embodiment, the oligonucleotide is covalently attached to the support using techniques well-known to those of skill in the art.

The nucleotide sequence of the oligonucleotide is complementary to a region, or segment, of the target nucleic acid sequence. The target nucleic acid sequence is also referred to herein as a template, which serves as a substrate for the enzymatic polymerization of a complementary nucleic acid strand. The oligonucleotide sequence need not have 100% identity with the target sequence, but must be of sufficient identity with a region of the target sequence so that it anneals to, or hybridizes with the target. The oligonucleotide is also referred to herein as a primer, or oligonucleotide primer. As used herein, a primer refers to an oligonucleotide which anneals to, or hybridizes with, a nucleic acid such as DNA or RNA and is capable of acting as a site of initiation of the synthesis or polymerization of a nucleic acid sequence complementary to a template sequence, in the presence of deoxynucleotide substrates and appropriate enzyme. The oligonucleotide in the PCR amplification reaction is typically between about five and about one hundred nucleotides in length and more typically about 10 to about 50 nucleotides in length. The oligonucleotide must have sufficient length to form a stable hybrid molecule (i.e., complex, or duplex of oligonucleotide annealed to target sequence). The oligonucleotide in the ligase chain reaction is longer, typically approximately one-half of the length of the target nucleic acid sequence.

The distal end of the optical fiber with the oligonucleotide attached is contacted with the test sample containing the target nucleic acid sequence and contact is maintained under conditions suitable for the amplification of the target sequence. The amplification reaction can be either polymerase chain reaction, or ligase chain reaction. In both embodiments, the amplification reaction typically encompasses the following steps: denaturing double-stranded nucleic acid molecules to produce single-stranded nucleic acid molecules; annealing the single-stranded nucleic acid molecules to oligonucleotides; and finally, producing double-stranded target nucleic acid molecules, also referred to herein as the amplification product. (In the ligase chain reaction, the annealing and producing of double-stranded target sequence occur substantially simultaneously). These steps are repeated, or cycled, a sufficient number of times to result in detectable quantities of amplification product.

In the first step of the amplification reaction, the target nucleic acid in the test sample is maintained under conditions resulting in the production of single-stranded target nucleic acid molecules. Typical denaturing conditions are described herein and are also well-known to those of skill in the art.

In the second step of the amplification reaction the single-stranded target nucleic acid sequence in the test sample anneals to the immobilized oligonucleotide in a sequence-specific manner to form a stable hybrid molecule. Typical annealing conditions are described herein and are also well known to those of skill in the art. (See, for example, MOLECULAR CLONING, Sambrook, J. et al., Cold Spring Harbor Laboratory Press, 1989; CURRENT PROTOCOLS IN MOLECULAR BIOLOGY, eds. Ausuble, F. M., et al. Wiley and Sons, Inc. (1993), the teachings of which are incorporated herein by reference).

If the amplification reaction is by the polymerase chain reaction, the nucleotide sequence of the oligonucleotide primer typically is complementary to a region of nucleotide sequence that flanks, or borders the target nucleic acid sequence (the sequence to be amplified). Pairs of primers can be used in the polymerase chain reaction amplification where each primer of the primer pair is complementary to a different region of the target nucleic acid sequence. Typically, one primer of the pair is directed to the positive strand (coding strand) of a double-stranded target nucleic acid, and the other primer of the primer pair is directed to the negative strand (anti-coding strand) of the double stranded target.

In the third step of the amplification reaction, the hybrid molecule is maintained in the presence of one or more polymerase enzymes and deoxyribonucleotide triphosphates under conditions suitable for the polymerase to enzymatically extend, or elongate, the oligonucleotide sequence along the length of the target nucleic acid (also referred to as a template), resulting in a double-stranded target nucleic acid molecule.

If the amplification reaction is by ligase chain reaction, the oligonucleotide (referred to herein as the first oligonucleotide) immobilized on the optical fiber is typically complementary to a region of the target nucleic acid sequence, and is more typically complementary to about one-half of the target nucleic acid sequence (e.g., the left half of the target sequence). In this step of the ligase chain amplification reaction, the test sample is maintained in the presence of a second oligonucleotide. The sequence of the second oligonucleotide is typically complementary to a region of the target nucleic acid sequence that is immediately contiguous with, or adjacent to, the sequence complementary to the first oligonucleotide (e.g., the right half of the target). The contact of the target nucleic acid is maintained under conditions suitable for the target sequence to anneal to the first oligonucleotide and for the second oligonucleotide to anneal to the target, resulting in hybrid molecules. Also present are one, or more, ligases that covalently link the adjacent first and second oligonucleotides, resulting in a double-stranded target nucleic acid molecule. In both embodiments, these steps are repeated for a sufficient number of cycles to obtain a detectable quantity of amplification product.

In another embodiment of the present invention, a pair of oligonucleotides is immobilized on the solid support. For example, a pair of oligonucleotide primers (e.g., primer (a) and primer (b)) can be used, with the nucleotide sequence of each primer complementary to a different region of the target nucleic acid sequence. Typically the different regions of the target sequence are at opposite ends of the target sequence. During the annealing step of the amplification reaction, a single-stranded target nucleic acid molecule, which has been formed by the elongation of primer (a), comprises a region of sequence (b) at the opposite end of the strand. Because this single-stranded target sequence is still immobilized on the solid support, and if a second primer is present on the solid support with a sequence complementary to sequence (b), the end of this target sequence will anneal to primer b, and a target molecule will form that is attached to the solid support at both ends. This molecule essentially forms a "bridge" between primer (a) and primer (b). Thus, multiple target sequences can be readily detected simultaneously because the amplification products are "captured" on the support and cannot dissociate back into solution and possibly escape detection.

The method further comprises the step of monitoring the support for the presence of one or more amplification products in which one or more amplification products are indicative of the presence of one or more target sequences and in which absence of an amplification product is indicative of the absence of a target sequence. The formation of a plurality of amplification products allows the detection of a plurality of target nucleic acid sequences.

Optical fibers provide a preferred support. Use of optical fibers allows for the optical detection of detectably labeled amplified target nucleic acids, as well as providing solid support. The optical fiber may optimally be coated with a material that has light-altering properties such as, for example, light scattering, light absorbing, light reflecting or light filtering properties. Examples of such material would be glass, silica or plastic. Light-altering properties of the optical fiber can include light scattering with distributed reflective/absorptive particles; light absorbing with opaque materials or absorbtive dyes; light reflecting with metal films or particles, high refractive index discriminators, opaque materials or reflective coatings; and light filtering with dichraic mirrors, optical dyes or gels/colloids with wavelength-sensitive scattering.

Another embodiment of the optical fibers of the invention employs layering the amplified product with the materials described immediately above to facilitate signal detection. These materials may have the light-altering properties described above, such as light reflecting properties or focusing properties. For example, an additional layer such as a membrane or filter can cover (overlay) or reside underneath (underlay) the immobilized amplification product which can alter, or modify, the accessibility of chemical reagents in solution to the distal surface of the support, and/or the amplified product. Alternatively, the layer can alter, or modify, the rate of formation of the amplification product.

Alternatively, the surface of the optical fiber may be contoured or shaped in such a way as to facilitate optical focusing properties. The light refracting/light reflecting properties of concave and convex surfaces is well known to those of skill in the art.

Typically, the amplification product incorporates a label capable of detection. These labels include agents such as radioisotopes, chemiluminescent, luminescent, photoabsorbing, electrochemiluminescent and fluorescent agents. The term "agents" is used in a broad sense in reference to labels, and includes any molecular moiety which participates in reactions which lead to a detectable response. Where the amplification product participates in hybridization reactions to form a further hybridization product, such product can be detected with intercalating agents.

Agents well known to those of skill in the art that can be used during PCR is, for example, detectably labeled deoxynucleoside triphosphates (e.g., dNTPs such as dATP, dGTP, dCTP and dTTP). These agents are enzymatically incorporated directly into the elongating nucleotide sequence, resulting in a detectably labeled amplification product. Such labeled dNTPs are commercially available, or readily produced by standard laboratory procedures by one of skill in the art.

Alternatively, a detectably labeled moiety which stably binds to, or hybridizes with the amplification product, either during the amplification reaction cycles, or after cessation of the amplification reaction (typically immediately after cessation) can be used. The detectable label can be as described above. The moiety can be any substance that binds to or hybridizes with nucleic acids. Such substances are well known to those of skill in the art and can include, e.g., fluorescent dyes, intercalating agents, nucleic acid probes (defined herein as a nucleic acid sequence having a sequence complementary to a target nucleotide sequence), nucleic acid analogs (e.g., inosine), nucleic acid binding proteins, antibodies and chelating agents.

In a further embodiment of the present invention, a support is used with oligonucleotides directed to different target nucleic acid sequences, for the substantially simultaneous detection of more than one target nucleic acid sequence. Typically, each oligonucleotide (pairs of oligonucleotides can also be used) is positioned in a discrete area of the support. The configuration of the support can be, for example, a solid support with a planar surface. Each area of the support may contain a plurality of primer pairs for amplification of a plurality of target sequences contained in a test sample. This embodiment of the present invention, also referred to herein as multiplex amplification, can be used to provide rapid and accurate detection of a panel, or group of target sequences important for diagnosis of a disease. A single test sample from a patient can contain different pathogenic organisms, each of which can require different reagents for detection. For example, the target sequences can comprise nucleic acid sequences from different types, or strains of bacteria or parasites, to diagnose infection. Multiplex amplification permits the substantially simultaneous amplification of nucleic acids from different organisms in a single assay and obviates the need to do multiple, individual assays. The multiplex embodiment of the present invention is particularly convenient in doctor's offices and small clinics when rapid diagnosis is required.

Optionally in this embodiment, at least one pair of oligonucleotides is a "nonsense" sequence pair. The nonsense sequence is not complementary to any target sequence and does not generate an amplification product, thus serving as a negative control for the reaction. Additionally, at least one oligonucleotide pair is a "positive control" pair having a sequence which is known to be present in the test sample, thus serving as a positive control.

Another embodiment of the present invention, as described herein, is useful for mapping nucleic acids of considerable length. In this embodiment, amplification products formed will span overlapping sequences of the target nucleic acid. These overlapping sequences can be correlated to produce a map of the target nucleic acid. The present invention may be used preferentially to replace the use of sequence tag sites by using an array of amplification products.

In yet another embodiment of the present invention a method is disclosed which facilitates the formation of a precipitate or agglutination product following the amplification of a target sequence. This method features a first support with one oligonucleotide attached to it, and a second support with a different oligonucleotide attached to it. The method comprises forming contacting the first and second supports with the test sample under conditions suitable for amplification of the target nucleic acid sequence, if present in the test sample. The amplification process promotes an agglutination or precipitation of the amplification product on the solid supports. This embodiment of the present invention preferably used beads, or particles as the solid support.

The methods of the present invention can be used to detect genetic abnormalities, such as mutations that are associated with specific diseases such as cystic fibrosis, Tay Sachs disease, sickle cell anemia, or a genetic marker for cancer such as mutated BRCA1. These methods can also be used to detect viral, bacterial and yeast nucleic acids from pathogenic organisms indicative of infection. They can also be used in forensic medicine and to assay the purity of solutions and compounds, e.g., intravenous solutions or drugs. The methods of the present invention can also be used to detect the presence of DNA/RNA damage or repair. For example, DNA covalently attached to an optical fiber is exposed to a suspected carcinogen for a sufficient period of time for the carcinogen to induce lesions in the DNA. The damaged DNA is then exposed to repair enzymes and the amount of incorporation of detectably labeled nucleotides is directly assessed on the tip of the fiber.

Also encompassed by the present invention is a kit for detecting the presence of a target nucleic acid sequence in a test sample comprising a support surface, an optical fiber, or bundle of fibers, with one, or more oligonucleotides attached to the fiber which can be used to produce detectable amplification products containing the target sequence. Alternatively, the kit can comprise a solid support, for example, for multiplex amplification reactions. For example, the kit can comprise a carrier such as a compartmentalized box, which holds one or more containers. The containers can be vials or receptacles to hold lyophilized or solution materials, e.g., detectably labeled deoxynucleoside triphosphates, detectably labeled moieties, enzymes such as polymerases or ligases, buffers and optical fibers with immobilized oligonucleotides. The kit could also include a sheet of paper, or a booklet containing instructions regarding the use of the kit components. Such a kit would be suited for multiple assays, e.g., a 50 test kit, for target nucleic acid sequences (i.e., a multiple use kit). Alternatively, the kit can comprise only enough reagent for a single assay (i.e., a single use kit).

Also encompassed in the present invention is a kit comprising a support surface where the surface has already been treated, or prepared to facilitate attachment of the oligonucleotide. For example, a flat support surface can be chemically treated to attach an intermediate chemical that is used to covalently attach the oligonucleotide to the surface. In this embodiment, the end-user can easily attach specific oligonucleotides and customize the amplification reaction.

The methods of the present invention are well suited for automation. A further embodiment of the present invention features an apparatus, or instrument for detecting a target nucleic acid sequence in a test sample. The apparatus comprises means for receiving a solid support having an immobilized oligonucleotide with a nucleotide sequence complementary to a region of sequence of the target as described above. The apparatus further comprises means for contacting the test sample with the support. The apparatus further comprises means for forming an amplification product (e.g., providing conditions suitable for denaturing, annealing and amplifying nucleic acids, either by polymerase chain reaction or ligase chain reaction, and detection of the amplification product.

Means for producing amplification products comprise devices such as, for example, dispensing orifices, pipettes for contacting reagents with the test sample. Typical reagents can include, for example, polymerases, ligases, nucleotides and buffers.

Thus, the present invention provides methods and apparatus for the detection of target nucleic acid sequences without using solution based oligonucleotides/primers, which eliminates the need for an electrophoretic gel-based system for the analysis of amplified products and facilitates the analysis of the assay results, thereby greatly reducing the time to generate data necessary to detect nucleic acids.

BRIEF DESCRIPTION OF THE DRAWINGS

FIGS. 1A through 1M depict schematically a method and apparatus for detecting a target nucleic acid sequence when the solid support is in a bead configuration.

DETAILED DESCRIPTION OF THE INVENTION

Figure 1E:
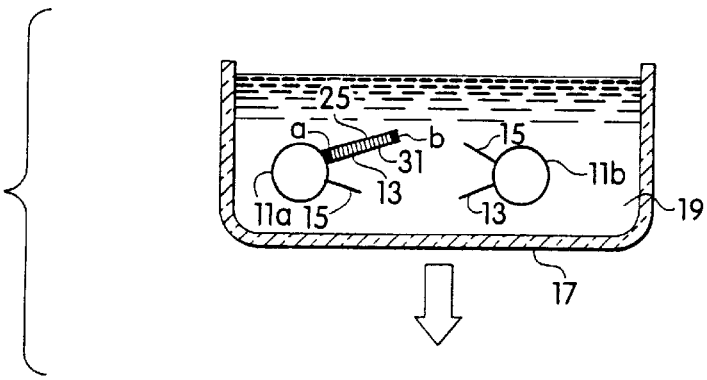

The present invention relates to methods, apparatus and kits for detecting the presence of a target nucleic acid sequence in a test sample. Specifically, the methods and apparatus described herein encompass the use of a solid support for the amplification and optical detection of a target sequence. The use of a solid support in the amplification reactions of the present invention results in an amplification product that remains captured on a support such as an optical fiber or surface. A number of advantages result from the use of a solid support. The amplification reaction is localized to a small area of the support resulting in a greater signal to noise ratio and better detection than with conventional solution based amplification reactions. Separation of amplification products is not required in order to detect a specific amplified target sequence in the present invention, as is required with conventional amplification reactions. Using the methods of the present invention, the detection of multiple target sequences is facilitated because multiple amplification reactions can take place in parallel on discreet areas of a surface. Finally, because the reaction products are captured on a support, detection of amplification products is also facilitated.

As used herein, the term support encompasses, for example, beads, particles, dipsticks, filters, membranes, silicon, silane or silicate supports such as glass and fibers. In one embodiment of the present invention the support comprises optical fibers. Preferably supports useful in the present invention comprise inert or inactive materials that do not react with components of the amplification reaction, or interfere with the amplification reaction. Such materials include, for example, epoxy silane, polystyrene, polycarbonate, polypropylene or other plastics, derivatized silica, nylon or latex. Alternatively, a material can be treated, or coated with inert materials.

The form, or configuration of the support can be, for example, in addition to fibers, a sphere, such as a bead or particle. In another embodiment of the present invention the support is a surface which can be flat, or planar, or can contain concave or convex areas. Such configuration would be particularly suited to provide for the analysis of multiple samples.

A particular support encompassed by the present invention comprises a sheet which has surfaces with alignment features to facilitate the precise positioning of nucleic acid sequences. This type of support allows for the delineation of areas of the support directed to two, or more distinct target sequences, e.g., a first target sequence and a second target sequence. These areas are preferably arranged in a grid type pattern of pixels.

The sample containing one or more target nucleic acid sequences, i.e., the nucleic acid sequences to be detected, is referred to herein as the test sample. The test sample encompasses any sample containing a nucleic acid sequence (DNA or RNA, double stranded or single stranded) capable of being amplified. For example, the target nucleic acid sequence can be of mammalian, specifically a human, origin such as a gene, gene fragment or gene product. The target nucleic acid sequence can also be of bacterial, viral, parasitic or yeast origin. The test sample can comprise any sample that contains nucleic acid sequences, for example, biological fluids such as blood, urine, cereberal spinal fluid, semen, saliva, stool or perspiration. The test sample can also comprise whole or lysed cells, or tissue such as biopsy material. Also encompassed by this invention are test samples which are to be tested for the presence of nucleic acid sequences as contaminates, such as nucleic acid sequences resulting from bacterial contamination in, for example, chemical extracts and distillates and other suspensions or colloids.

A review of the figures will facilitate the understanding of the present invention. FIGS. 1A through 1M depict an article of manufacture, a plurality of carboxylated latex beads, generally designated by the numerals 11a and 11b, for making an amplification product. The presence of an amplification product will be used to indicate the presence of complementary target sequences of a first nucleic acid. As used in the following illustrations, the term "first nucleic acid" refers to the target nucleic acid sequence to be detected. Latex beads 11a and 11b have at least one second nucleic acid, (also referred to herein as an oligonucleotide and as a primer) and preferably, a plurality of copies of second nucleic acids which will act as primers in an amplification reaction. The second nucleic acid is immobilized, e.g. covalently through a 5' linkage and the carboxylated functional group of the latex bead. As illustrated, each latex bead 11a and 11b has a second nucleic acid 13 and a third nucleic acid 15 for purposes of simplicity, with the understanding that many more second and third nucleic acids 13 and 15 may be present on each support. The representations of the latex beads 11a and 11b and second and third nucleic acids 13 and 15 are for illustrative purposes and are not drawn to scale.

The methods of the present invention can be performed manually or in an automated instrument. Each FIG. 1A to 1M represents a stage of the amplification reaction.

In FIG. 1A, latex beads 11a and 11b are depicted as being suspended in an aqueous solution 19 contained within a vessel 17. Solution 19 and/or beads 11a and 11b are dispensed into vessel 17 by a dispensing orifice 21 or may be prepackaged in vessel 17.

FIG. 1B illustrates the addition of a first nucleic acid 23 derived from a sample, to vessel 17. First nucleic acid 23 may be placed in vessel 17 prior to beads 11a and 11b or after as illustrated. First nucleic acid 23 may be placed in vessel 17 by means of any suitable dispenser, such as orifice 21 depicted in FIG. 1A. First nucleic acid 23 is double stranded DNA, comprising a first strand 25 and a second strand 27. Each strand has two complementary copies of the target sequence, a and b. Second nucleic acid 13 is complementary to target sequence a of strand 25 and homologous to sequence a of strand 27. Third nucleic acid 15 is homologous to target sequence b of strand 25 and complementary to sequence b of strand 27. First nucleic acid 23 and latex beads 11a and 11b form a reaction product.

FIG. 1C depicts the reaction product, latex beads 11a and 11b and first nucleic acid undergoing denaturation conditions. Denaturation conditions are imposed at this stage by suitable means such as controlling temperature, and/or ionic strength, and/or the pH of solution 19 contained in vessel 17.

The reaction product, comprising the first nucleic acid and the latex beads 11a and 11b, is next subjected to annealing conditions as represented in FIG. 1D. Annealing conditions are achieved by adjusting one or more factors influencing annealing, including temperature, and/or ionic strength and pH.

FIG. 1D depicts an annealed, or hybridization product comprising first nucleic acid strand 25 and second nucleic acid 13 of latex bead 11a. First nucleic acid strand 27 may also have target areas [not shown] which interact with further primers [not shown]. For purposes of simplicity and clarity, this discussion will focus on strand 25 and target sequence a and b.

The annealed product, comprising first nucleic acid stand 25 and second nucleic acid 13 of latex bead 11a, is next subjected to elongation, or extension, conditions, as represented in FIG. 1E. Elongation conditions are preferably imposed by adding suitable reagents for elongation of a nucleic acid, including a thermal-stable polymerase, such as Taq polymerase (other polymerases are well-known to those of skill in the art), nucleotides and other necessary reagents, such as buffers. The elongation reaction can take place in a vessel 17 and suitable reagents can be added through orifices such as orifice 21 depicted in FIG. 1A. FIG. 1E depicts a first elongation product as 31 covalently extended from first nucleic acid 13. This product is complementary to the target sequence of first nucleic acid strand 25. Thus elongation product 31 has a target sequence b which is complementary to third nucleic acid 15 of latex beads 11a or 11b.

Figure 1F:
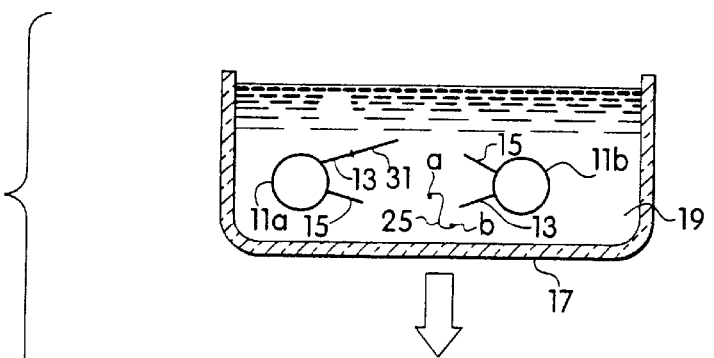

The first elongation product is next subjected to denaturation conditions, as illustrated in FIG. 1F. Upon imposition of denaturation conditions, a denaturation product is formed comprising first nucleic acid strands 25 and 27; second and third nucleic acids 13 and 15 of latex beads 11a and 11b; and a first elongation product 31 as illustrated in FIG. 1F. Denaturation conditions comprise elevated temperatures, higher salt concentrations and/or lower pH. An orifice 21 depicted in FIG. 1A can be used for adding reagents or heating elements [not shown].

Figure 1G:
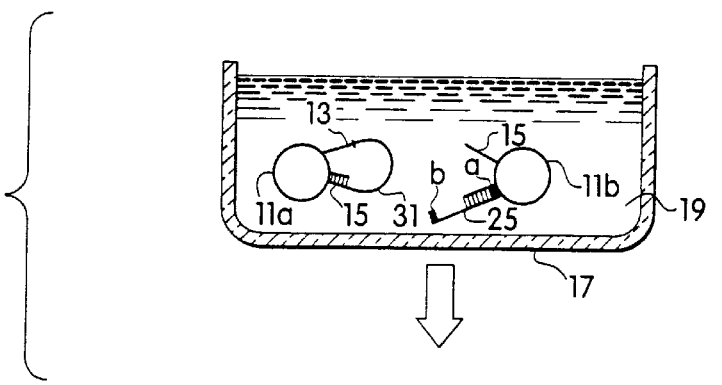

The denaturation product is next subjected to annealing conditions as illustrated in FIG. 1G. Upon imposition of annealing conditions, an annealed product is formed. In one alternative, as illustrated in FIG. 1G the annealed product comprises the first elongation product 31 and third nucleic acid 15 of latex bead 11a; and the first nucleic acid strand 25 and second nucleic acid 13 of latex bead 21b.

Figure 1H:
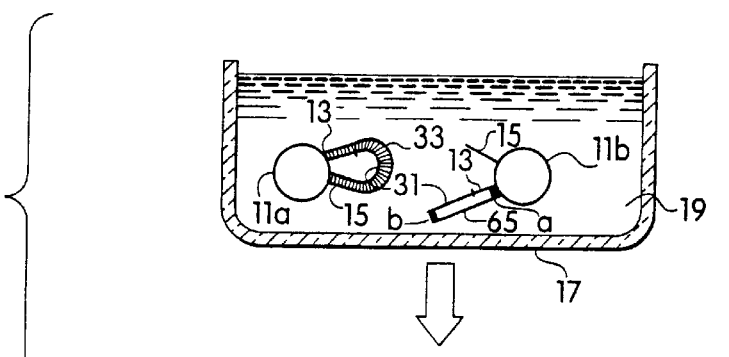
Figure 1I:
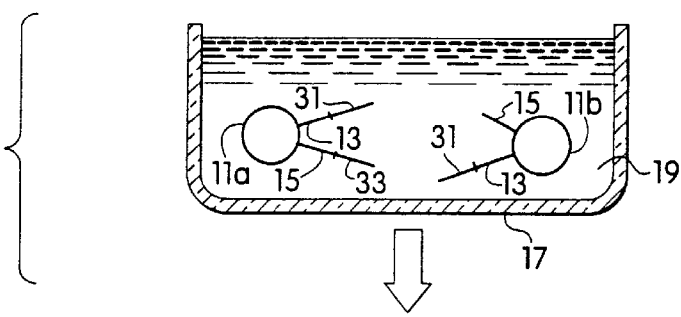
Figure 1J:
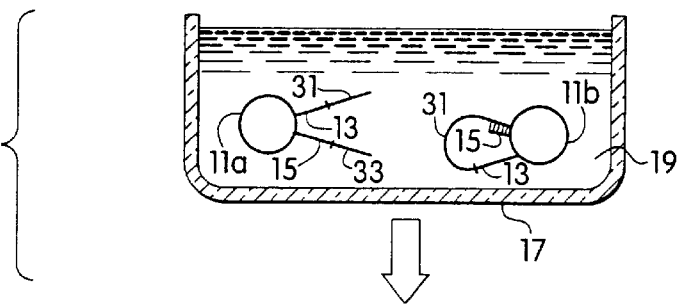
Figure 1K:
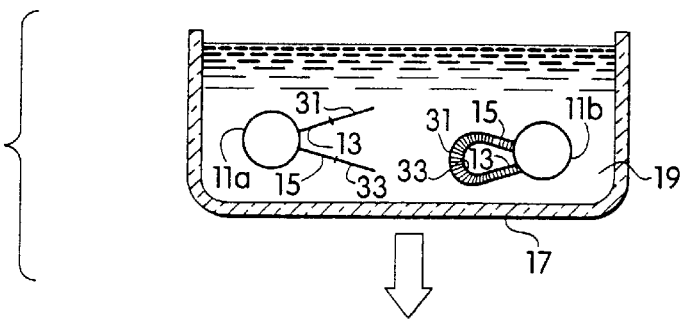
Figure 1L:
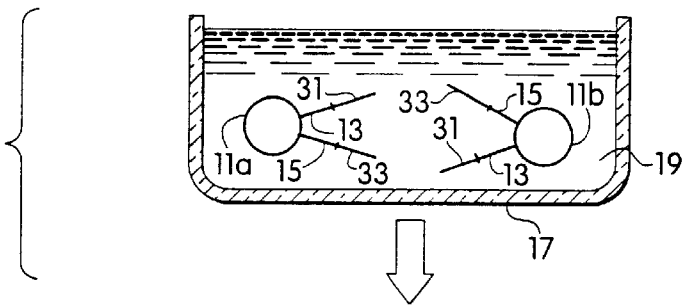

Upon imposition of elongation conditions, as illustrated in FIG. 1H, a second elongation product 33 is formed. The second elongation product extends from third nucleic acid 15 of latex bead 11a. In the alternative, a second elongation product 33 is formed extending from third nucleic acid 15 of latex bead 11b. A further first elongation product 31 is formed from first nucleic acid 13 of latex bead 11b.

Imposition of further cycles of denaturation, annealing, elongation and denaturation as depicted in FIG. 1I–FIG. 1L, form additional first and second elongation products 31 and 33 extending from each second and third nucleic acid 13 and 15 of each latex bead 11a and b. These cycles can be repeated as many times as desired until the second and third nucleic acids 13 and 15 are exhausted.

Figure 1M:
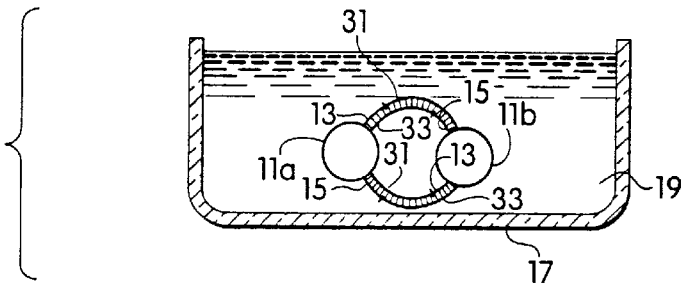

First and second elongation products 31 and 33 anneal to each other and facilitate annealing between adjacent latex particles, forming a bridge 11a and 11b, as depicted in FIG. 1M. The annealing of first and second elongation products 31 and 33 on adjacent latex beads 11a and 11b disrupts the suspension and the beads 11a and 11b precipitate or agglutinate into a detectable mass. Preferably, this detectable mass is detected by monitoring equipment [not shown]. The formation of the detectable mass is indicative of the presence of the first nucleic acid and, in particular, target sequences a and b of strand 25.

Turning now to FIGS. 2A through 2J, and in particular, an apparatus, generally designated by the numeral 111, for making an amplification product in the presence of a first nucleic acid, is depicted. The apparatus can comprise an epoxy silane derivatized support 113. The support has an upper surface 117 with two primer anchoring areas 121 and 123. Areas 121 and 123 each contain a primer pair comprising a second and a third nucleic acid. The second and third nucleic acids of area designated 121 are designated 125 and 127 respectively. The second and third nucleic acids of area 123 are designated 125' and 127' respectively. The representations of the nucleic acids and areas 121 and 123 are for illustrative purposes only and are not drawn to scale. The areas are preferably pixel sized. These areas are preferably areas of 10 $\mu^2$ to 1 mm$^2$.

The support 113 may take many different forms, such as sheets of glass, beads or fibers. Individuals skilled in the art can readily modify the shape and size of the support in order to fit individual needs. The entire support 113 may be any convenient size. For example, it can be shaped to present a planar upper surface 117 of approximately 1 cm$^2$.

Turning now to FIG. 2B, a sample, generally designated by the numeral 131, is contacted with the support 113 forming a reaction product. Thus, the test sample contacts the nucleic acids immobilized on areas 121 and 123. Sample 131 has a first nucleic acid 133 having target sequences complementary to the second nucleic acid of region 121 and 123. As depicted, means for applying the sample 131 to support 113 comprise a sample dispensing orifice 135. The methods of the present invention can be performed manually or in an automated instrument.

In another embodiment, the methods of the present invention can be performed in a self contained reaction cartridge. Typically, the cartridge contains all of the necessary reagents needed to perform the assay. The cartridge will have a port for introduction of the sample and separate isolated chambers for buffers, enzymes, and detection agents, e.g., dyes or labeled oligonucleotides. Microfabrication techniques facilitate production of supports for use in a cartridge, and in other configurations.

Turning now to FIG. 2C, annealing conditions on imposed on the reaction product. Upon imposition of annealing conditions, an annealed product is formed in area 121 comprising a first nucleic acid 133 and a second nucleic acid 125. Annealing conditions may comprise altering the ionic strength or pH of solutions, or lowering temperature in order to effect the hybridization of the first and second nucleic acids. Means for imposing annealing conditions are depicted by reagent dispensing orifice 137 and cooling fan 139.

Turning now to FIG. 2D, elongation conditions are imposed on the annealed product, if present, to form a first elongation product. The first elongation product 145 comprises a nucleic acid extending from the second nucleic acid 125 corresponding to the first nucleic acid 133. Elongation conditions may comprise the addition of polymerases and proof-reading enzymes, nucleoside triphosphates, buffers and other reagents necessary to effect an elongation reaction.

Reagents to form a first elongation product 145 are dispensed through a dispensing orifice 143, or may already be present.

Figure 2E:
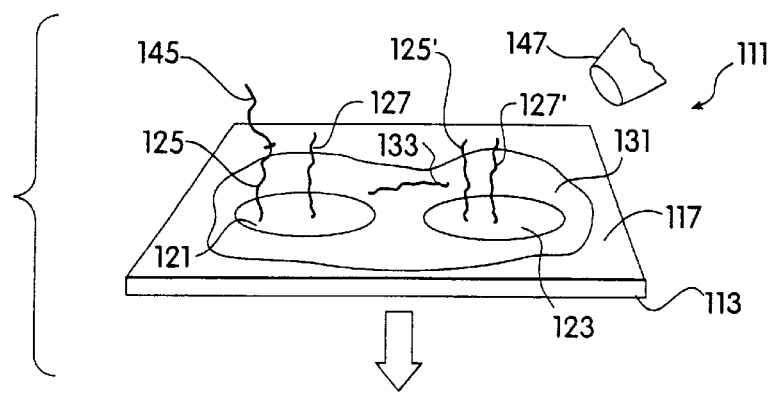
FIGS. 2A though 2L depict schematically a method and apparatus for detecting a target nucleic acid sequence when the solid support is a surface.

FIG. 2E depicts a stage where one or more functions may be performed. The nucleosides incorporated into the elongation product can be labeled in order to effect detection. Thus, this stage may comprise detection means [not shown] to monitor the support 113 for the presence of the elongation product. However, for most detection formats, it is useful to provide additional elongation products to increase signal. Thus, denaturation conditions are imposed on the elongation product 145 to allow first nucleic acid strand 133 to disassociate from second nucleic acid 125 and first elongation product 145. Denaturation reagents can be dispersed on support 113 through orifice 147.

Figure 2F:
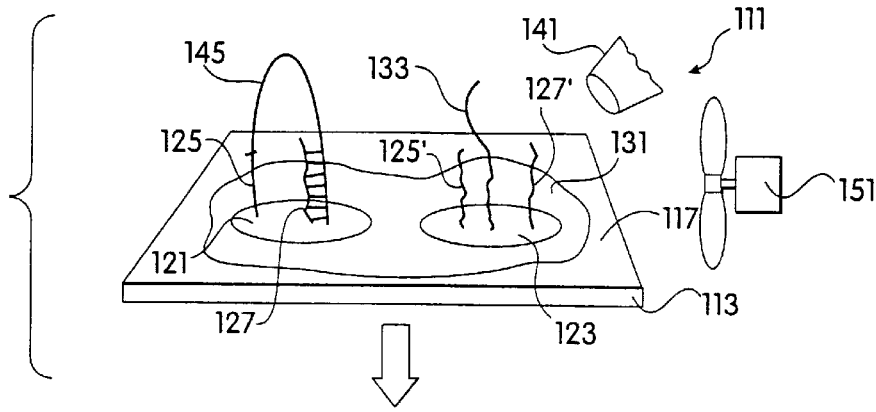

Additional signals can be obtained by again forming additional hybridization products. Turning now to FIG. 2F, a second annealed product is formed. In the event that the test sample has not been removed, the first nucleic acid 133 may still remain to anneal with nucleic acid 125' of area 123 to effect a further first annealed product. With respect to the area 121, a second hybridization product is formed between the first amplification product 145 and third nucleic acid 127. Means for imposing annealing conditions have been described previously.

Figure 2G:
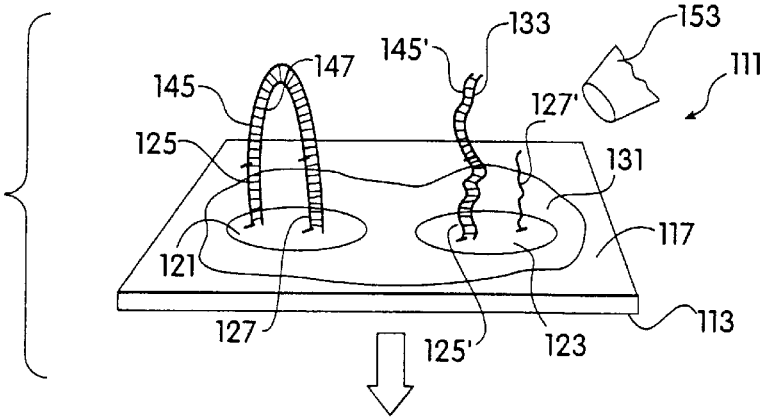

FIG. 2G depicts forming a second elongation product 147 in area 121 and a further first elongation product 145' in area 123. Upon imposition of elongation conditions, a second elongation product 147 is formed in the first region 121. The second elongation product 147 comprises a nucleic acid which is complementary to the first elongation product 145. The second elongation product 147 extends from the third nucleic acid 127. A further first elongation product 145' is formed in the second area 123 extending from second nucleic acid 125'. Amplification reagents can be applied to support 13 by dispensing orifice 153.

Figure 2H:
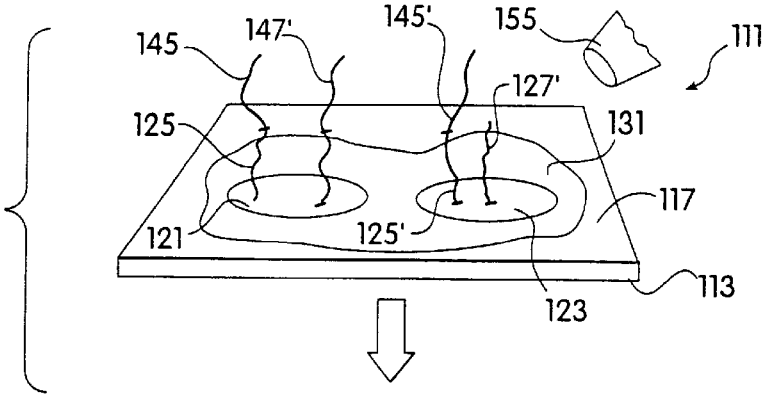

Moving now to FIG. 2H, denaturation conditions are imposed. After denaturation, a first and second elongation product 145 and 147 extend from the second and third nucleic acid 125 and 127 of area 121, and a first elongation product 145' extends from second nucleic acid 125' of region 123. Means for imposing denaturation conditions are depicted generally by dispensing orifice 155 and by heating elements [not shown].

Figure 2I:
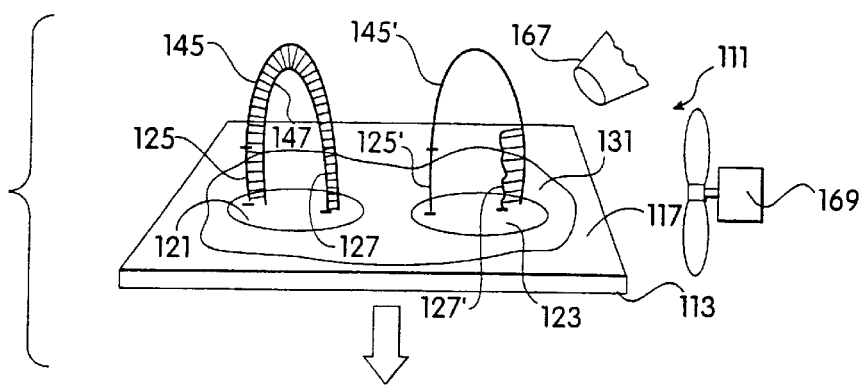

Turning now to FIG. 2I, annealing conditions are imposed on the support 113. Upon imposition of annealing conditions, the first and second elongation products 145 and 147 of area 121 hybridize to each other; and, the first elongation product 145' of region 123 hybridizes to the third nucleic acid 127'.

Figure 2J:
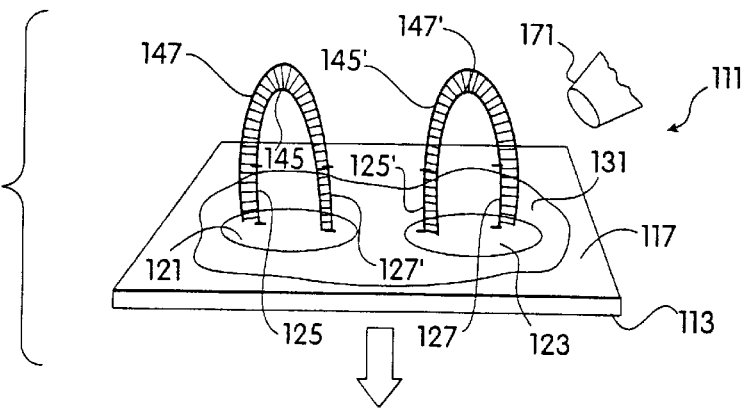

Turning now to FIG. 2J, elongation conditions are imposed upon the support 113. Upon imposition of amplification conditions, a second elongation product 147' is formed comprising a nucleic acid extending from third nucleic acid 127' which is complementary to the first elongation product extending from second nucleic acid 125'. Means for imposing amplification conditions comprise amplification reagents applied through dispensing orifice 174. Amplification reagents comprise buffers, salts, enzymes, nucleotides and the like.

Figure 2K:
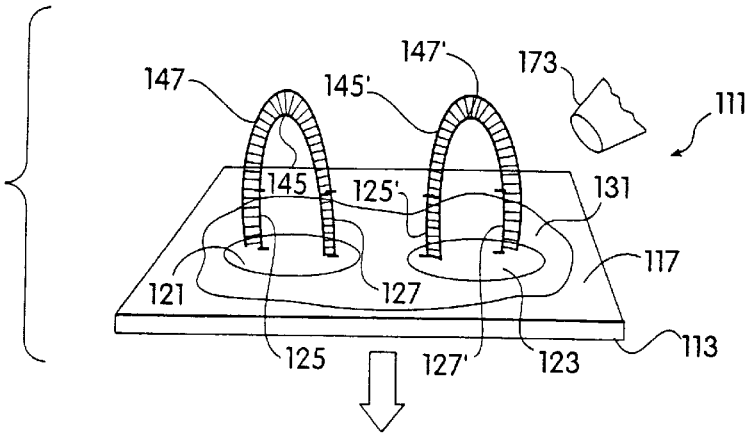

Turning now to FIG. 2K, washes can optionally be applied to remove unincorporated nucleosides and extraneous matter which may interfere with signal. As illustrated, a wash dispensing orifice 173 applies wash reagents and solutions to the support 113.

Figure 2L:
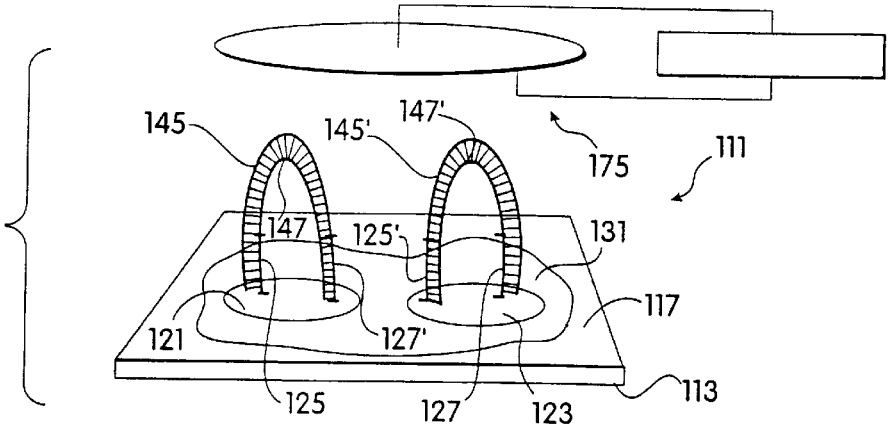

FIG. 2L, represents a detection step, in the event the method is used for diagnostic or detection purposes rather than for the synthesis of nucleic acid. Detection means 175 detects labelled nucleosides, if such nucleosides are used to form elongation products 145, 145', 147 and 147'. Detection means can comprise photosensors to detect chemiluminescent, luminescent and fluorescent or radioactive labels. Additional reagents to develop the signal are applied to the support 113.

In the event that the first and second elongation products are made with labeled nucleosides, upon imposition of detection conditions, such as the addition of cofactors or light of a wavelength to which the label is sensitive, a signal can be developed indicating the presence of the first nucleic acid.

In the alternative, annealing conditions can be applied to the support in the presence of intercalating agents to develop a signal in the presence of the first and second elongation products. In addition, a fourth labeled oligonucleotide [not shown] complementary to the first or second elongation product can be used as a probe for detecting the presence of the target first oligonucleotide.

As illustrated, area 121 and 123 have identical second and third nucleic acids 125 and 127 or 125' and 127'. However, support 113 preferably has a plurality of areas which are directed to a plurality of targets. Preferably, at least one area comprises a second and third nucleic acid which have nonsense sequences. This area is not intended to produce a signal, but to serve as a negative control. The presence of a signal from such second and third nucleic acids defining nonsense sequences indicates a system error.

Preferably, at least one area has a second and third nucleic acid which have sequences that correspond to a first nucleic acid, the presence of which is confirmed as being universally present or which is added to the sample. This area is intended to produce a signal in each instance as a positive control. The absence of a signal indicates a system error.

The nucleic acid amplification technique described above with reference to FIGS. 2G and 2J, for example, is sometimes referred to herein as "bridge amplification".

Figure 3:
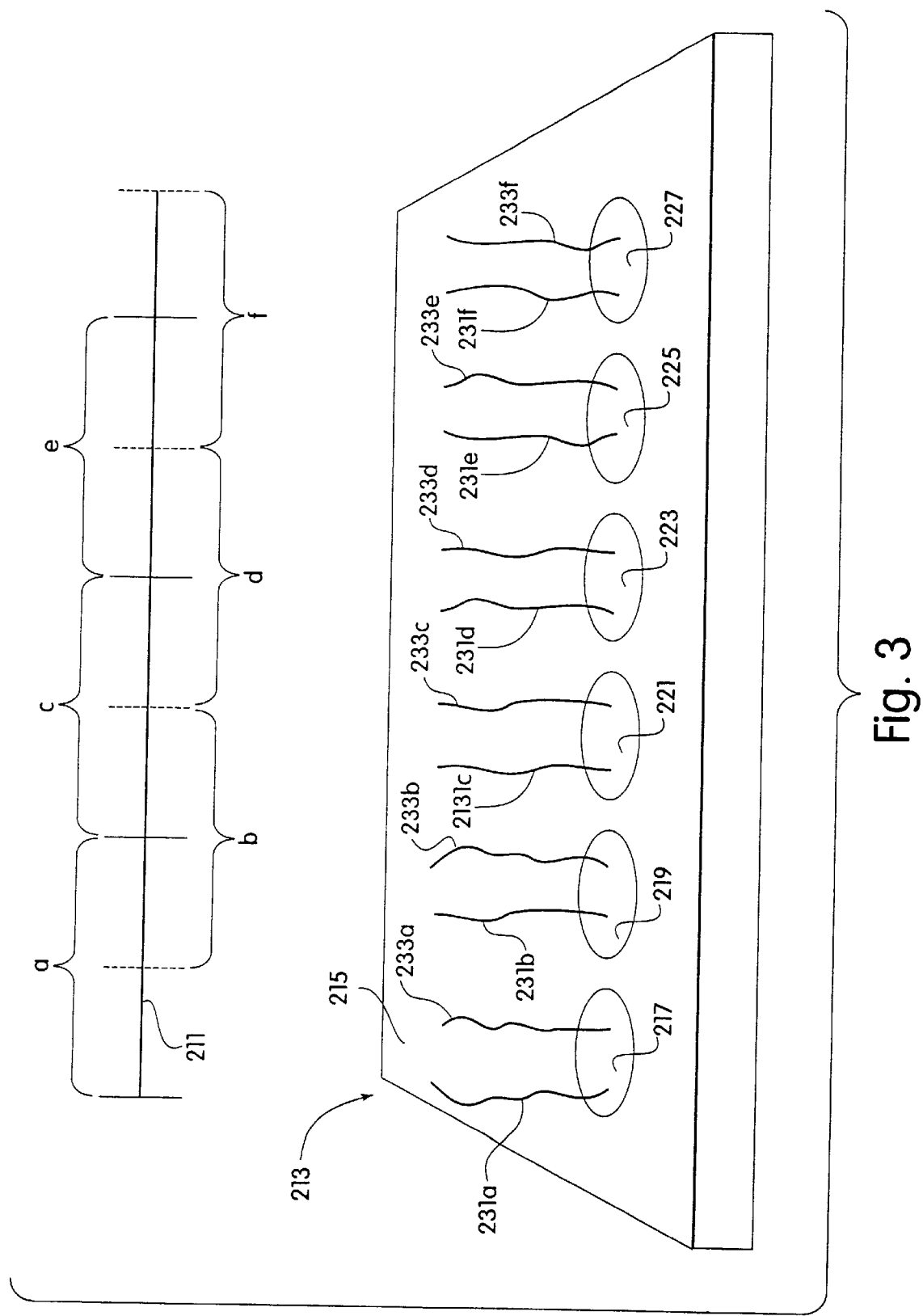
FIG. 3 depicts an apparatus for mapping regions of a nucleic acid.

Turning now to FIG. 3, a first nucleic acid generally designated by the numeral 211, is depicted. The first nucleic acid 211 has areas a through f located along its length. The device 213, for mapping regions of a first nucleic acid, has a flat surface 215. The surface 215 has areas 217, 219, 221, 223, 225 and 227.

Each area 217 through 227 has a second nucleic acid 231*a–f* respectively and a third nucleic acid 233*a–f* respectively. The second and third nucleic acids 231*a–f* and 233*a–f* of each area correspond to an area a–f of nucleic acid 211. Thus, the detectable signal of a particular area on support 215 will depend on the extent to which an area a–f of nucleic acid 211 presents itself. For example, a nucleic acid 211 comprising segments b, c and d, will be detected on areas 219, 221 and 223.

In operation, the device 213 is processed generally in accordance with the method described with respect to FIGS. 1A–1L. That is, a first nucleic acid 211, or alternatively, fragments of nucleic acid 211, are applied to one or more devices 213. The devices are monitored to detect the presence of an elongation product in areas 217, 219, 221, 223, 225 and 227.

A Surface as the Solid Support

According to one embodiment of the present invention, target nucleic acid sequence in a test sample is amplified, detected, and can be quantified, using pairs of primers attached to a surface contacting the sample and, optionally, other chemical reagents. Each pair of primers is homologous to complementary ends of the length of target sequence. When amplification conditions are imposed, amplified target nucleic acid sequence, also referred to herein as polynucleotide, is formed and attached to said surface by extension from the primers so attached. Because the primer pair is specific to the test sample target sequence, surface bound amplificate forms only if the target sequence is present in the test sample. The amplificate so formed can be detected conveniently by optical means if the amplificate is so labeled. Labeling techniques include: using labeled polynucleotides in the PCR mixture, including in the mixture a probe which is specific to the amplificate of the target sequence, and is detectable after being hybridized to said amplificate, or adding such a detectable probe after the amplification phase of the analysis is complete. A variety of labeled probes for such purposes is known within the art. The optical signal if present can be detected by a variety of known optical detection techniques, including photodiodes, photomultipliers, television cameras, CCD arrays, etc. When the detection scheme is fluorescence of a fluorogenic substance, such fluorescence can be induced by irradiating the surface bound amplificate with excitation radiation, including from an incandescent lamp, a discharge lamp, a laser, or other irradiation means known within the art. The amplification process may be localized to a given area by attaching the primer pair only at a given area, such that the surface bound amplificate only forms there, and the resultant optical signal is localized and may be detected at the predetermined location.

As an extension to the above, multiple target sequences within the test sample can be tested for by independently attaching multiple primer pairs in different areas of the said surface. Each primer pair is homologous to a given target sequence within a single length of sample polynucleotide, or to target sequences in two or more lengths of polynucleotide in the test sample. After amplification conditions have been imposed, and optionally the simultaneous or subsequent hybridization of an optically detectable oligonucleotide is effected, the presence or absence of multiple different target sequences can be detected from the presence or absence of optical signals from the appropriate localized areas of said surface. It is particularly advantageous to position the localized primer pairs on the surface such that the optically detectable labeled amplificate is formed into a group that is easily detected by optical schemes able to detect spatially distinct optical signals. Means of detecting such multiple optical signals in parallel include imaging the optical pattern onto an area sensitive optical detector such as a television camera, or CCD array, or other scheme known within the art. Alternatively, the pattern of multiple optically detectable signals may be detected sequentially, such as by individually imaging each signal in turn onto a detector also including detectors such as photodiodes, photomultipliers and other known detection means. Alternatively, this may be achieved by masking the optical signals with one or more spatial filters, and sequentially permitting each individually to be detected by the optical detector.

The surface to which the primer pairs are bound can advantageously be flat, or cylindrical, or spherical for ease of optical detection, or can conform to any other shape as my be chosen. Also, advantageously, said surface may be transparent, such that the optical signals may be detected through the transparent materials, and/or a fluorescent excitation signal may be applied through the transparent material. The ends of individual glass fibers, or of a bundle of glass fibers, may also serve as the surface to which said primer pairs may be attached.

Additionally, the surface or the optical fiber can be modified in various ways to enhance optical properties and signal detection. For example, layers or membranes can overlay or underlay the support surface resulting in light-altering effects. In the case of an optical fiber, the fiber can be shaped or contoured to enhance signal detection.

Furthermore, the surface to which the primer pairs are bound may be heated and/or cooled to effect thermocycling as part of the amplification conditions. Heating may be effected by known techniques such as applying heated material to the material whose exposed surface has primers attached, applying electrical joule heating, applying electrical peltier heating, applying electromagnetic radiation, and other known techniques. Cooling may be effected by applying cooled material, by applying electrical peltier cooling, by permitting the adiabatic expansion or evaporation of a liquid, conduction of heat away from the surface into the test sample, and other known techniques. Furthermore, means may be included for detecting the temperature of the surface, and/or of test sample within the vicinity of the surface, with such means including on the surface or its vicinity temperature sensing means, including thermocouples, thermistors, resistance thermometers, semiconducting devices, temperature sensitive optical elements, temperature sensitive magnetic materials, thermal expansion devices, and other known temperature sensing devices.

Such temperature sensing means may be combined with aforesaid heating and cooling means to effect temperature control by means well known to those of skill in the art. Alternatively, using techniques known to those of skill in the art, such as thermcouplers, the support surface, or optical fiber itself can control temperature, e.g., heating and cooling, in a manner sufficient to achieve the required denaturation, annealing and extension conditions for the amplification reaction.

Materials to which the primers may be attached include glasses, quartz, plastics, metals, ceramics, and other materials that are compatible with the amplification chemistry, including inert materials that do not chemically interact or release chemicals into solution. Alternatively, the surface may be coated with a material that modifies its properties in advantageous ways for attaching primers, or for permitting the amplification reaction to proceed without chemical modification or interference.

Said test sample may be an aqueous solution, or a gel, or an emulsion, or a colloidal solution, or a biological sample such as blood or any body fluid, or a sample derived from a body fluid, or biological tissue, or a soil extract, or a collected water sample, or generally any type of sample capable of containing one or more lengths of polynucleotide.

Optical Fibers as the Solid Support

The use of optical fibers and optical fiber strands in combination with light energy absorbing dyes for medical, biochemical and chemical analytical determinations has undergone rapid development, particularly within the last decade. The optical fiber strands employed are often glass or plastic extended rods having a relatively small cross-sectional diameter. When light energy is projected into one end of the fiber strand, the angles at which the various light energy rays strike the internal surface are greater than the critical angle; and such rays are "piped" through the strands length by successive internal reflections and eventually emerge from the opposite end of the strand. Typically, bundles of these strands can be used collectively as optical fibers in a variety of different applications.

For making an optical fiber into a sensor, one or more light energy absorbing dyes are attached to the distal end of the fiber. The sensor can then be used for both in vitro and/or in vivo applications. As used herein, light energy is photoenergy and is defined as electromagnetic radiation of any wavelength. Accordingly, the terms "light energy" and "photoenergy" include at least infrared, visible, and ultraviolet wavelengths conventionally employed in most optical instruments and apparatus.

Typically, light from an appropriate energy source is used to illuminate one end of an optical fiber or a fiber bundle. The light propagates along the length of the optical fiber; and a portion of this propagated light energy exits the opposite end of the optical fiber and is absorbed by one or more light energy absorbing dyes. As conventionally known, the light energy absorbing dye may or may not be immobilized; may or may not be directly attached to the optical fiber itself; may or may not be suspended in a fluid sample containing one or more analytes of interest to be detected; and may or may not be retainable for subsequent use in a second optical determination. Alternatively, reactants may be immobilized on the distal end of the fiber, (i.e., the end opposite that initially illuminated) where a reaction takes place resulting in the incorporation of a fluorophore which generates light energy which can be transmitted in the direction of the proximal end of the fiber (i.e., the end which is initially illuminated). These immobilized reactants may also contain light altering properties,. e.g., light reflecting, light scattering, light refracting and/or light absorbing. Materials such as, for example, glass, silica or plastic can be used in the present invention. Finally, the surface of the optical fiber may be either convex or concave in order to enhance optical focusing properties. In any of these embodiments, once light energy has been absorbed or incorporated, some light energy of varying wavelength and intensity typically travels through the optical fiber and is then conveyed through either the same fiber or a collection of fibers to a detection system where the emerging light energy is observed and measured, or, alternatively, is detected elsewhere. The interactions between light energy and light absorbing dyes both in the presence of a fluid sample containing one or more nucleic acids of interest provide an optical basis for both qualitative and quantitative spectral determinations.

A variety of light image processing and analytical systems have been developed in order to enhance, analyze, and mathematically process the light energies introduced to and emerging from the light absorbing dyes in such optical analytical techniques.

Typically, these systems provide components for image capture, data acquisition, data processing and analysis and visual presentation to the user. Several systems are commercially available from sources such as Quantex, Inc. and Spex Industries, Inc. Each of these systems may be combined with microscopes, cameras, and/or television monitors for automatic processing of all light energy determinations.

In one embodiment of the present invention, a method is provided that utilizes a solid-phase primer-directed amplification process with fiber optic detection format. In this embodiment an optical fiber, having a distal end and a proximal end, is utilized with the amplification reaction being performed on the distal end of the fiber and transmission of the resultant signal occurring through the fiber, the proximal end of which is engaged with the detector. In practicing this aspect of the invention, nucleic acid primers which anneal to the target nucleic acid to be amplified are immobilized on the distal end of the optical fiber. The formation of elongation products the on the distal end of the fiber indicates that the sample contained target nucleic acid sequences.

The use of an optical fiber as the amplification support facilitates optical detection of amplified products, thus enabling analysis of amplification progress as the reaction proceeds using fluorescence or absorption techniques. Concurrent real-time analysis of amplification progress facilitates accurate quantification of target concentration in a sample. The optical fiber also serves as an integral component of the product detection system. Thus, the use of an optical fiber performs a three-fold function as the support for the amplification reaction, as a transmission means for the resultant signal and as a component of the detection system by transmitting this signal to the detector.

One end of the optical fiber (referred to hereinafter as the distal end) is cleaved, polished, and then chemically modified to provide a surface having attachment sites for nucleic acid primers. A number of surface modification methods suitable for this purpose are known to those of skill in the art. For example, organosilane coating of glass and silica surfaces, graft polymerization on polymer surfaces, and/or high voltage gas-plasma discharges may be used to effect modification of glass, silica or polymer surfaces. The surface of the fiber may also be modified to have a convex or concave curvature to facilitate optical focusing. Following modification, oligonucleotides are then attached to the surface of the distal end of the fiber. This process usually involves several steps, which may include one or more of the following:

a) Chemical treatment of the fiber surface to activate attachment sites for primer binding;

b) Chemical treatment of the oligonucleotides to activate the groups which will interact with the fiber surface sites;

c) Placing the modified fibers in contact with the oligonucleotides to allow immobilization reactions to occur; and d) Treatment and washing of the fiber surface to remove non-immobilized oligonucleotides, as well as any activation reagents or blocking groups that may interfere with the amplification reaction.

The specificity of the amplification assay is governed by the sequences of the oligonucleotides that are immobilized on the face of the distal end of the fiber. For most applications, a mixture of two specific synthetic oligonucleotide primers will be immobilized on the distal surface of the optical fiber, preferably by formation of covalent bonds with groups on the fiber surface. These olignucleotides will ordinarily be chosen to amplify a specific subsequence, or region, of the target nucleic acid, using primer design strategies similar to those used for conventional, solution phase PCR, and related techniques.

Primer attachment is carried out so that the 3' terminal sequences of the oligonucleotides (for most applications between 5 and 50 bases of sequence) are accessible and capable of serving as primers for template-dependent polynucleotide synthesis by a suitable polymerase enzyme. In addition, attachment is carried out so that the distance between adjacent oligonucleotides of opposite polarity on the surface of the support is less than the length of the target nucleic acid.

To detect, for example, nucleic acid amplification on the fiber optic support, the following steps are performed:

a) A test mixture is prepared containing the sample, template and primer dependent polymerase, and other reagents used for polymerase dependent nucleic acid synthesis. The latter category would include buffers, salts, polymerase cofactors, nucleoside triphosphates, and possibly additional polymerase stabilizing agents such as detergents and/or blocking proteins (i.e., bovine serum albumin).

Separate control mixtures lacking sample would serve as a negative control to provide background signal levels for evaluation of amplification success. Similarly, additional standard mixtures containing known amounts of previously characterized target nucleic acid could be prepared as positive controls, and as concentration standards for quantifying sample target levels.

b) The primer-modified distal surface of the optical fiber is placed in contact with the appropriate reagents, forming a reaction combination/mixture.

c) The distal surface of the fiber is then subjected to a cyclic amplification process, similar to that used for PCR. The steps for carrying out amplification are set forth below in steps c1–c3:

c1: Imposition of conditions suitable for denaturing target and immobilized elongation products;

c2: Imposition of conditions suitable for annealing single-stranded target or single-stranded immobilized elongation products to fresh, unextended immobilized amplification primers;

c3: Imposition of conditions that allow polymerase extension of the primer-template complexes formed in step 2 above. These three steps are repeated as often as necessary to achieve the desired degree of amplification.

d) The distal surface of the fiber is then assayed for the presence of amplified product using optical detection methods that employ light conveyed through the optical fiber support, or excitation through the optical fiber and detection elsewhere.

Methods for amplification reactions, i.e., repeated cycles of nucleic acid denaturation, annealing/reannealing and polymerase extension fall into two broad categories, i.e., those that operate on the entire contents of the reaction vessel, using a conventional programmable thermal cycler as commonly used in PCR; and/or modulation of the reaction pH to effect nucleic acid denaturation and rehybridization. Cyclic addition of base to the reaction vessel is used to raise pH above the denaturation point, followed by neutralization to a pH below this point. The second category of amplification reaction entails treatment of the distal face of the fiber only. In this case, the regulated heating and cooling of the distal face of the fiber is mediated by fiber-based apparatus and/or processes.

Several methods could be beneficially used. For example, modulation of the temperature of the distal fiber surface by light energy passing through the fiber may be employed. There are at least two possible implementations of this approach which are feasible. These include 1) direct stimulation of water vibrational absorption by IR light; and 2) indirect heating caused by visible irradiation of dye molecules that undergo efficient radiationless decay to generate heat. These could be present in a layer on the fiber surface, or they could be present in the solution containing the reaction mixture. Alternatively, resistive electrical heating caused by current passing through an electrically conducive layer deposited on the surface of the fiber may be employed. Finally, modulation of electrical potential (voltage) of the distal fiber surface to alternately effect denaturation and hybridization of the DNA may be used, such as with a thermocoupler.

Elongation products will be detected by means of light signals transmitted through the fiber. The proximal end of the optical fiber is connected to apparatus that allows optical detection of elongation products. The preferred apparatus will include some or all of the following features:

a) Means for detecting and measuring light intensity at the distal end of the fiber, i.e., light passing through the fiber toward the proximal end;

b) For methods involving fluorescence detection, a means for passing light of defined wavelength and intensity through the proximal end of the fiber, so as to illuminate the distal end of the fiber.

c) Means to allow simultaneous or substantially simultaneous operation of the detection and illumination steps described in (a) and (b) above. For fluorescence applications, a dichroic mirror may be employed to separate and filter the fluorescent signal returning from the sample from the excitation beam. Epifluorescence microscopes employ dichroic mirrors in a similar fashion.

A variety of optical detection strategies can be used in implementing the present invention. Product can be quantitated during or after amplification. Kinetic analysis of amplification progress may be performed concurrently with cycling, thus quantifying initial DNA target levels.

As amplification on optical fibers facilitates analysis of fluorescence-based detection, several fluorescent labeling techniques are contemplated for use in is practicing this aspect of the present invention. Elongation products can be labeled via the inclusion of fluorescently tagged nucleotide triphosphates in the reaction mixture. As polymerase mediated extension of DNA strands proceeds, fluorescently tagged nucleotides are incorporated. Therefore, the amount of product synthesized should be proportional to the fluorescent signal generated at the distal end of the fiber. Elongation products may also be detected using fluorescent DNA-specific dyes, i.e., ethidium bromide. Detection can be performed after amplification or concurrently with cycling. During concurrent detection, the dye is included in the reaction mixture. Fluorescence is recorded at the same point (and temperature) during each cycle (near the end of the amplification stage). A cycle dependent increase in fluorescent intensity indicates the accumulation of DNA on the fiber tip. In another embodiment, amplification may be detected using fluorescently labeled nucleic acid probes which hybridize specifically to amplified products attached to the distal end of the optical fiber. Fluorescence energy transfer probes that fluoresce only when hybridized may also be used to monitor product formation during cycling.

Finally, absorbance-based measurements of product accumulation may also be made using the optical fiber. The preferred apparatus would involve an external light source and follow the increase in absorbance during or after the amplification reaction. For instance, the absorbance of DNA bases at 260 nm or the absorption of nonspecific DNA-binding agents could be used to detect product on the distal end of the fiber since amplification of product would lead to the concentration of those agents on the fiber.

Description of Optical Configurations

The following optical configurations can be used to detect surface-attached optically detectable oligonucleotides (also referred to herein as polynucleotides). The configurations described herein can be used more generally for any chemical species which may be surface-attached and optically detected.

Figure 6A:
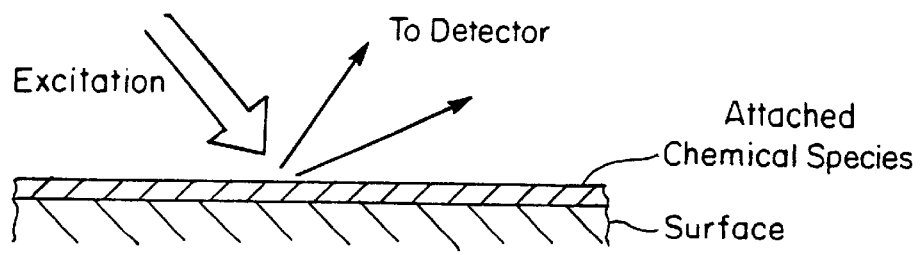
FIGS. 6A–6R depict amplification product detection schemes when the solid support is a surface.

The various optical configurations that can be used for detecting signals from optically detectable surface bound chemical species are illustrated by the examples that follow. The following descriptions apply to the drawings, FIGS. 6A–6R And FIGS. 7A–7M included herewith. FIGS. 6A–6R indicate configurations possible with surfaces with attached chemical species, and FIGS. 7A–7M illustrate more specifically additional configurations applicable to optical fibers and bundles of optical fibers.

Amplification on a Surface

FIG. 6A depicts the case where the surface with chemical species attached is illuminated by excitation optical energy, and the resultant optical signal is optically detected with a detector positioned such as to be able to capture such signal from the surface.

Figure 6B:
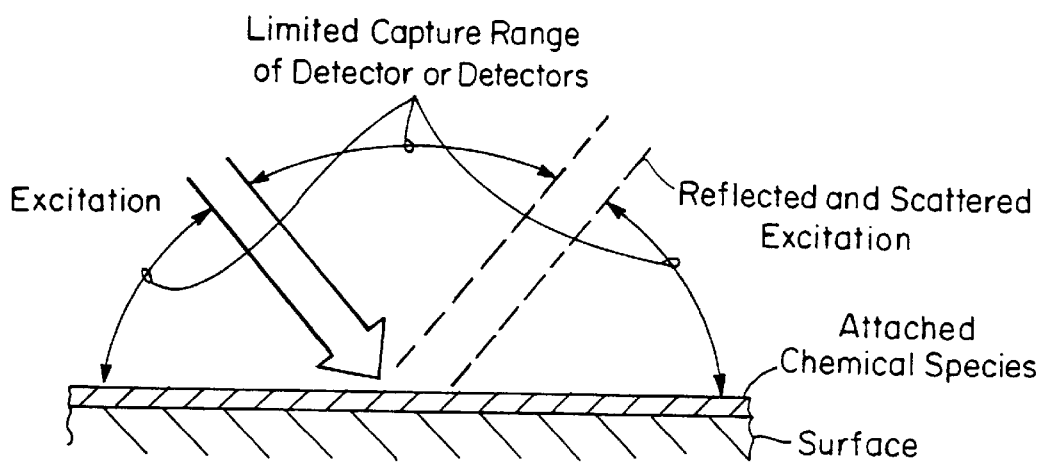

FIG. 6B depicts the case where the surface with chemical species attached is illuminated by excitation optical energy, and the resultant optical signal is optically detected with one or more detectors positioned such as to be able to capture such signal from the surface, but positioned such that all or much of reflected optical energy is prevented from entering the detector.

Figure 6C:
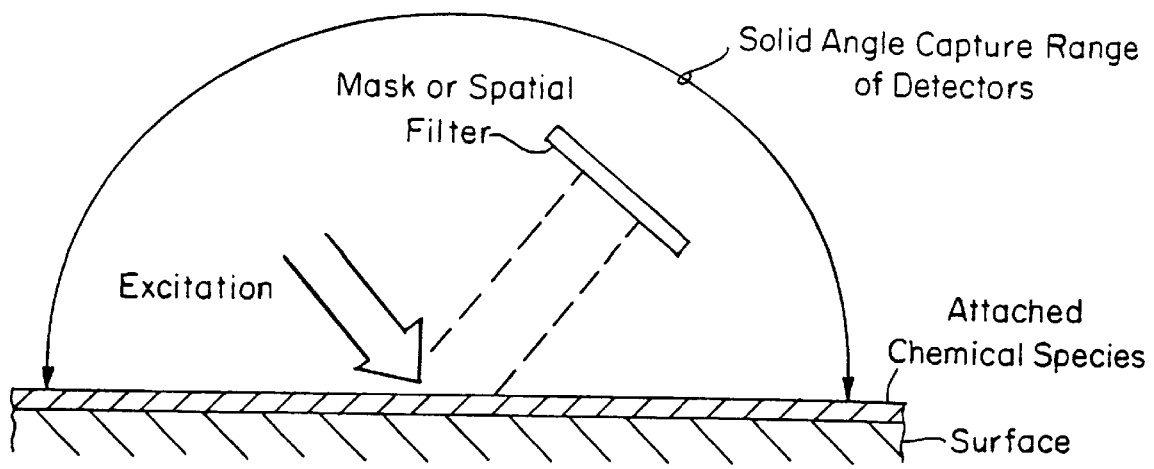

FIG. 6C depicts the case where the surface with chemical species attached is illuminated by excitation optical energy, and the resultant optical signal is optically detected with one or more detectors positioned such as to be able to capture such signal from the surface, but a mask or spatial filter is positioned to prevent all or much of the reflected optical energy from entering the detector.

Figure 6D:
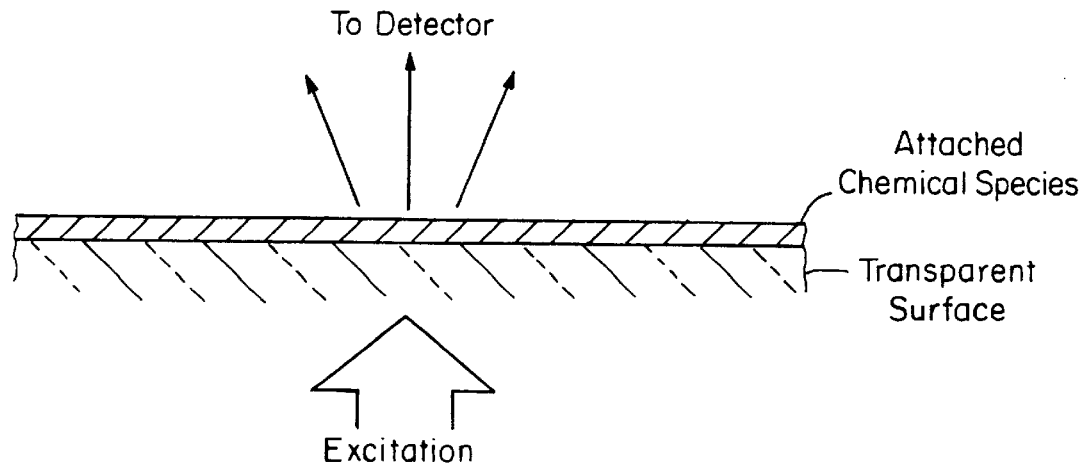

FIG. 6D depicts the case where the surface is transparent, such that it is optically accessible from both the side of the test sample where chemical species is attached, and also through the surface. Optical excitation is applied through the transparent surface and the detected signal is detected from the side to which the amplified chemical species is attached.

Figure 6E:
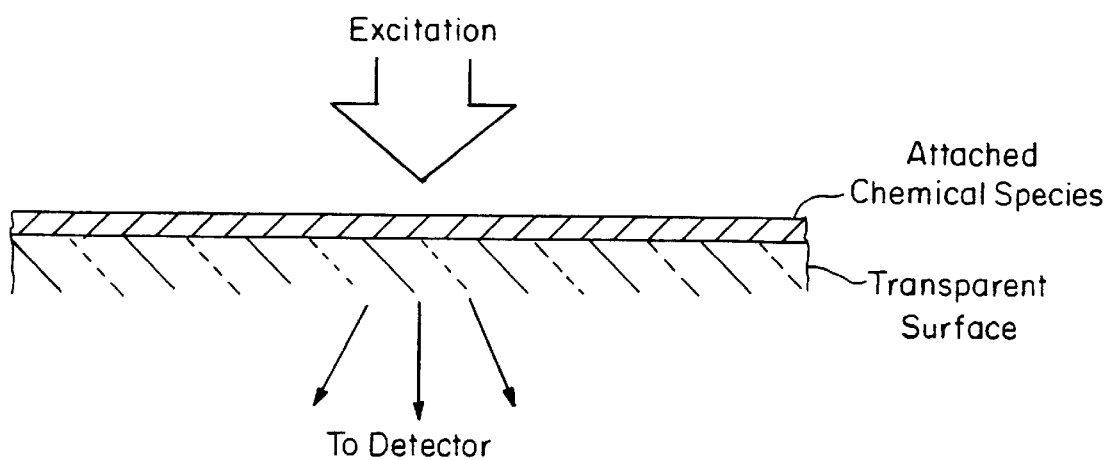

FIG. 6E depicts the case of a transparent surface where the optical excitation is applied to the surface attached chemical species and the detected signal is detected through the transparent surface.

Figure 6F:
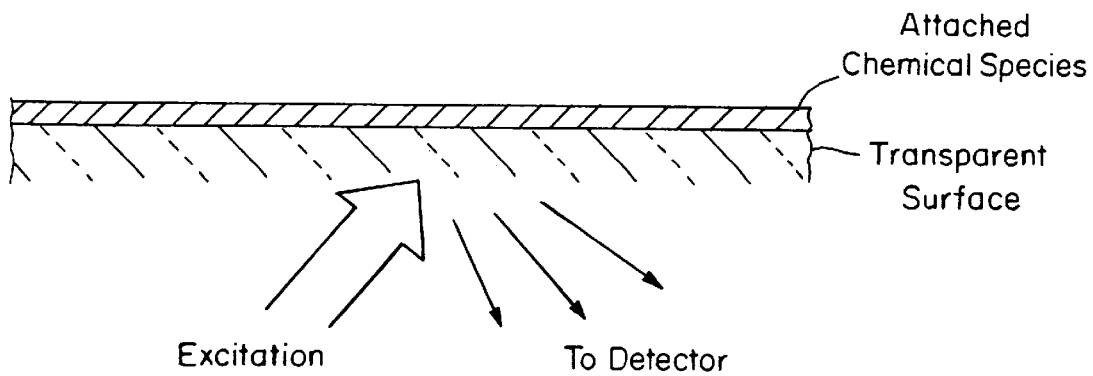

FIG. 6F depicts the case where the optical excitation is applied to the attached chemical species through the transparent surface and the optical signal is detected through the transparent surface.

Figure 6G:
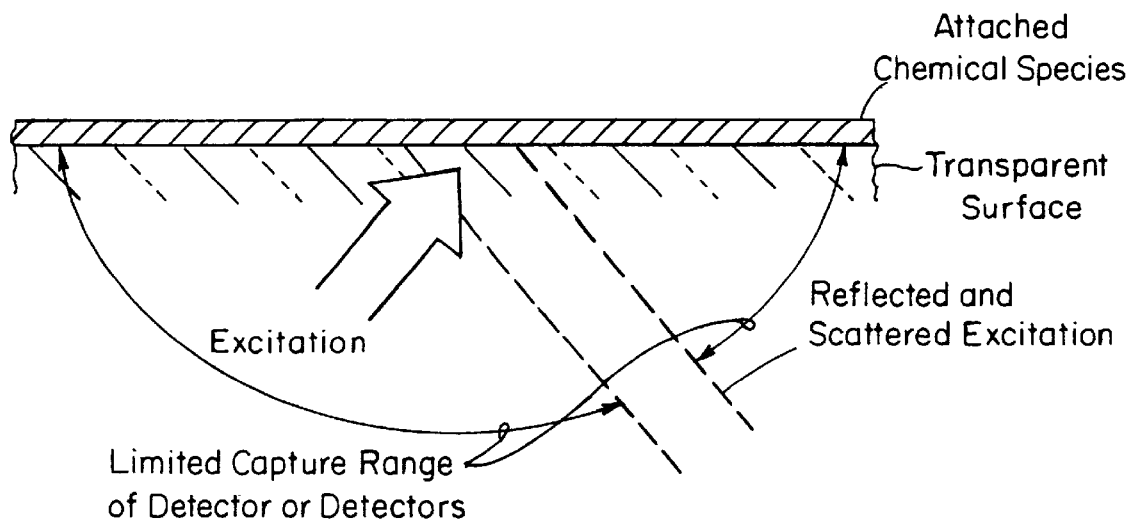

FIG. 6G depicts the case where the optical excitation is applied to the attached chemical species through the transparent surface and the optical signal is detected through the transparent surface, with the optical capture range of the detector being limited such that all or much of the reflected excitation energy does not enter the detector.

Figure 6H:
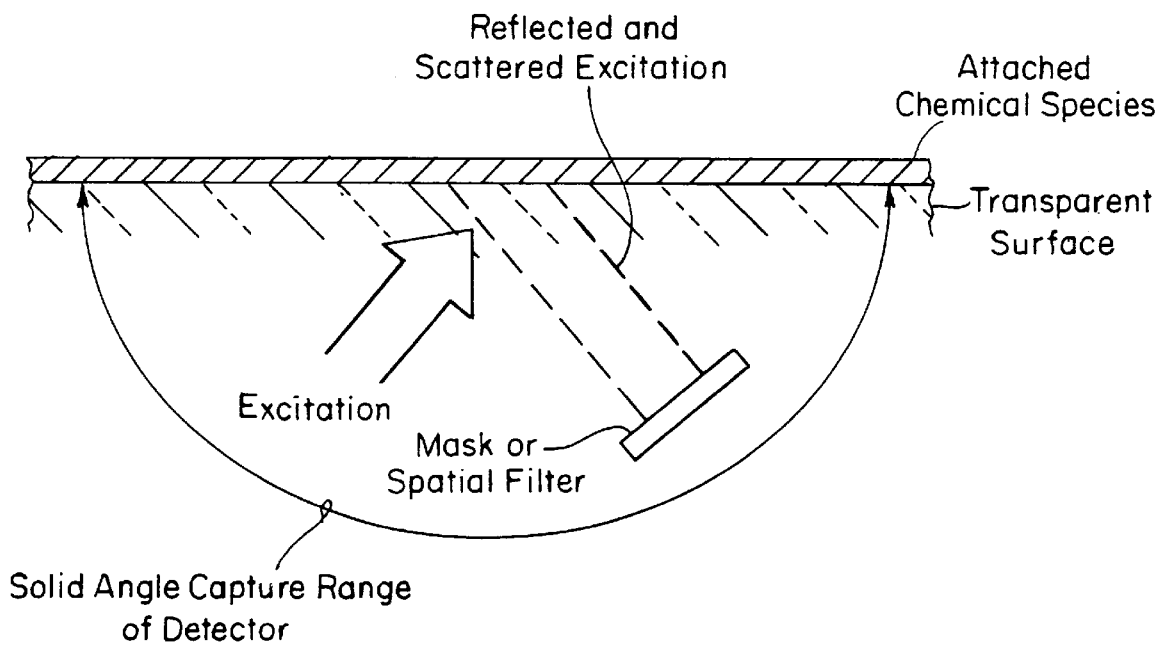

FIG. 6H depicts the case where the optical excitation is applied to the attached chemical species through the transparent surface and the optical signal is detected through the transparent surface, with a mask or spatial filter positioned to block all or much of the reflected excitation energy from entering the detector.

Figure 6I:
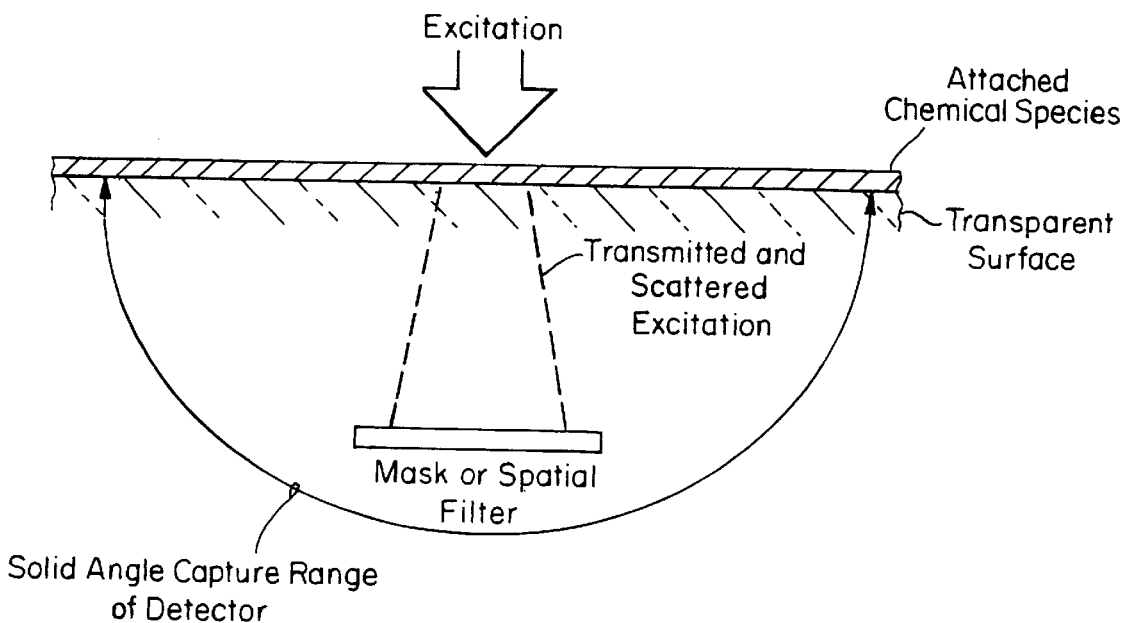

FIG. 6I depicts the case where the optical excitation is directly applied to the attached chemical species, and the detected signal from the attached chemical species is detected through the transparent surface, with a mask or spatial filter positioned to block all or much of the transmitted optical energy from entering the detector.

Figure 6J:
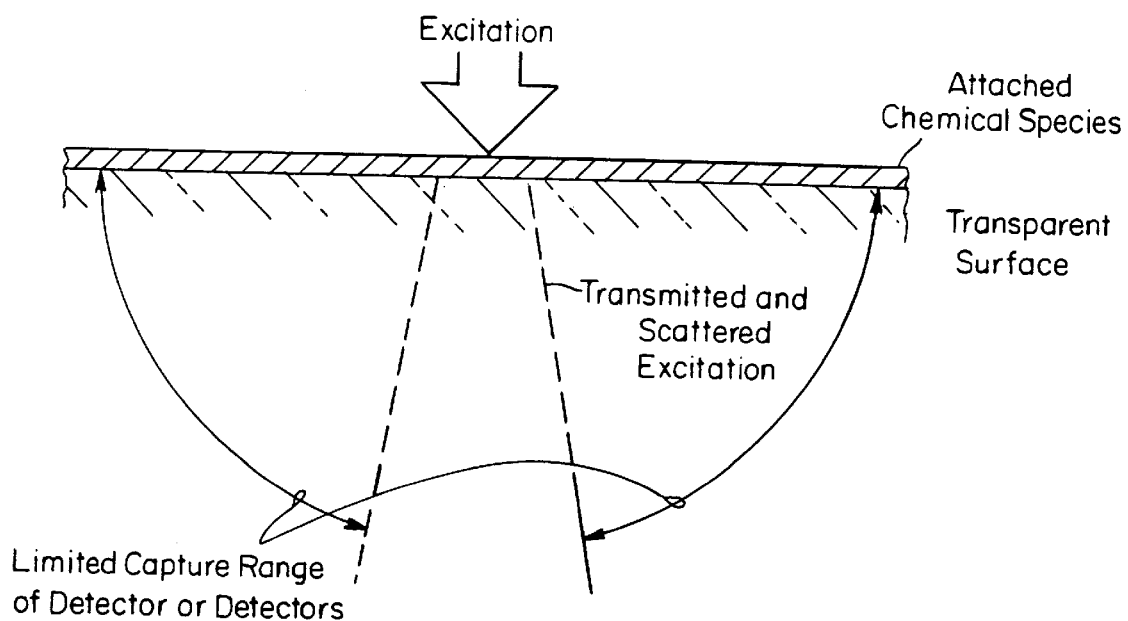

FIG. 6J depicts the case where the optical excitation is directly applied to the attached chemical species, and the detected signal from the attached chemical species is detected through the transparent surface, with the optical capture range of the detector being limited such that all or much of the transmitted optical energy does not enter the detector.

Figure 6K:
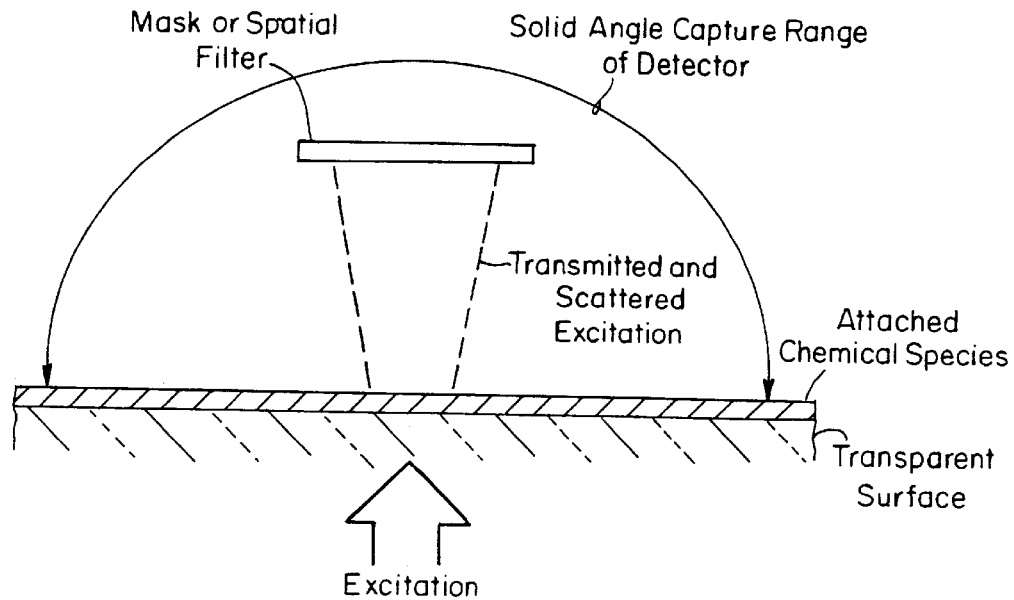

FIG. 6K depicts the case where the optical excitation is applied to the attached chemical species through the transparent surface, and the signal is detected directly from the attached chemical species, with a mask or spatial filter positioned to block all or much of the transmitted optical energy from entering the detector.

Figure 6L:
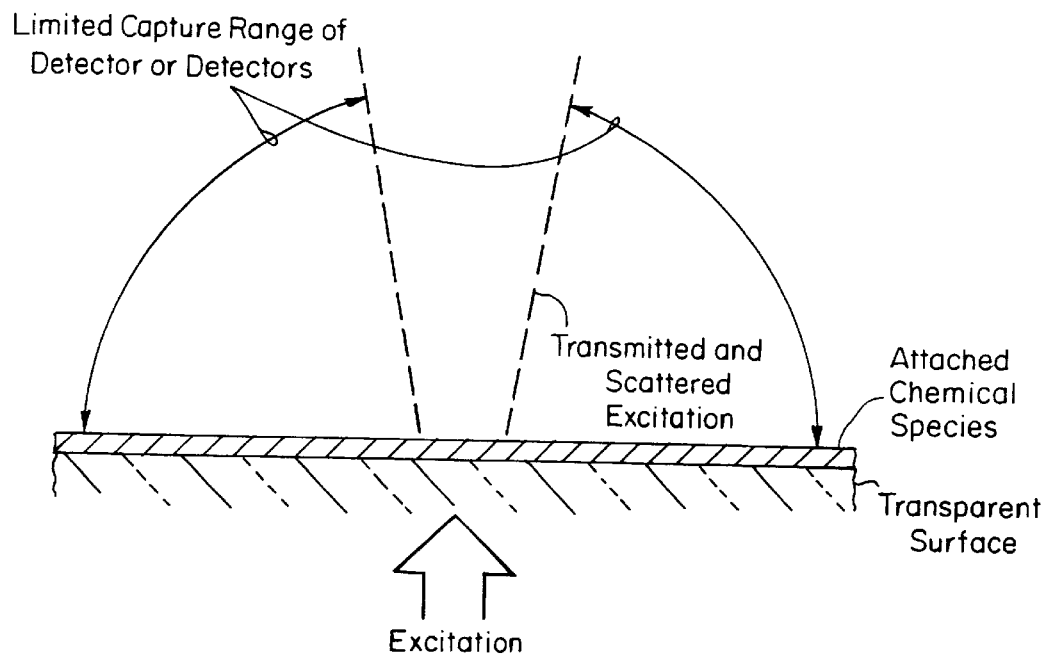

FIG. 6L depicts the case where the optical excitation is applied to the attached chemical species through the transparent surface, and the signal is detected directly from the attached chemical species, with the optical capture range of the detector being limited such that all or much of the transmitted optical energy does not enter the detector.

Figure 6M:
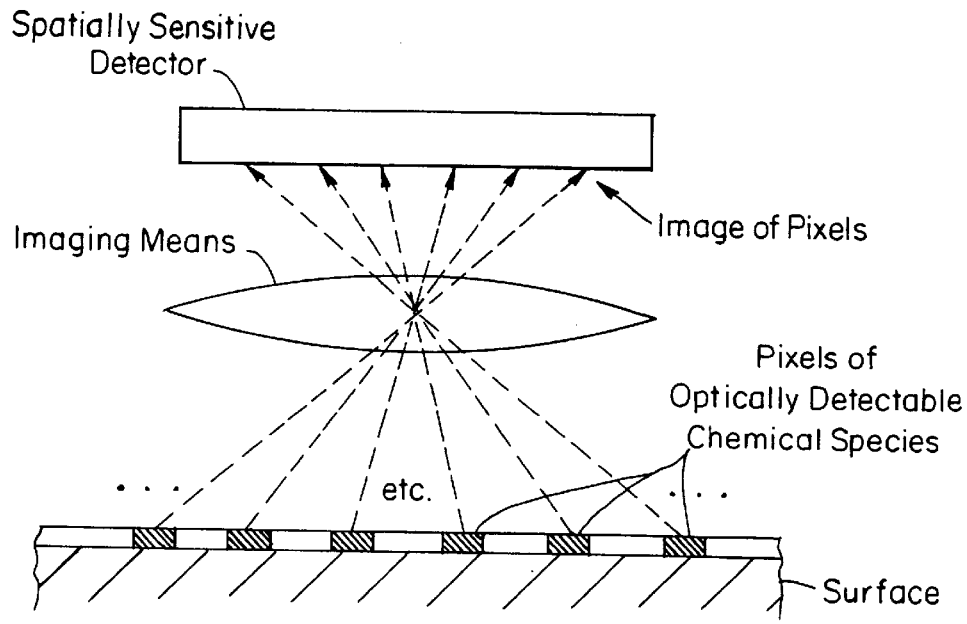

FIG. 6M depicts the case where multiple pixels of attached chemical species are positioned on the surface with a spatial relationship, and a lens or other imaging means forms an image of the multiple pixels on a spatially sensitive detector able to individually distinguish the imaged pixels such that the presence and image intensity of each pixel can be detected in parallel.

Figure 6N:
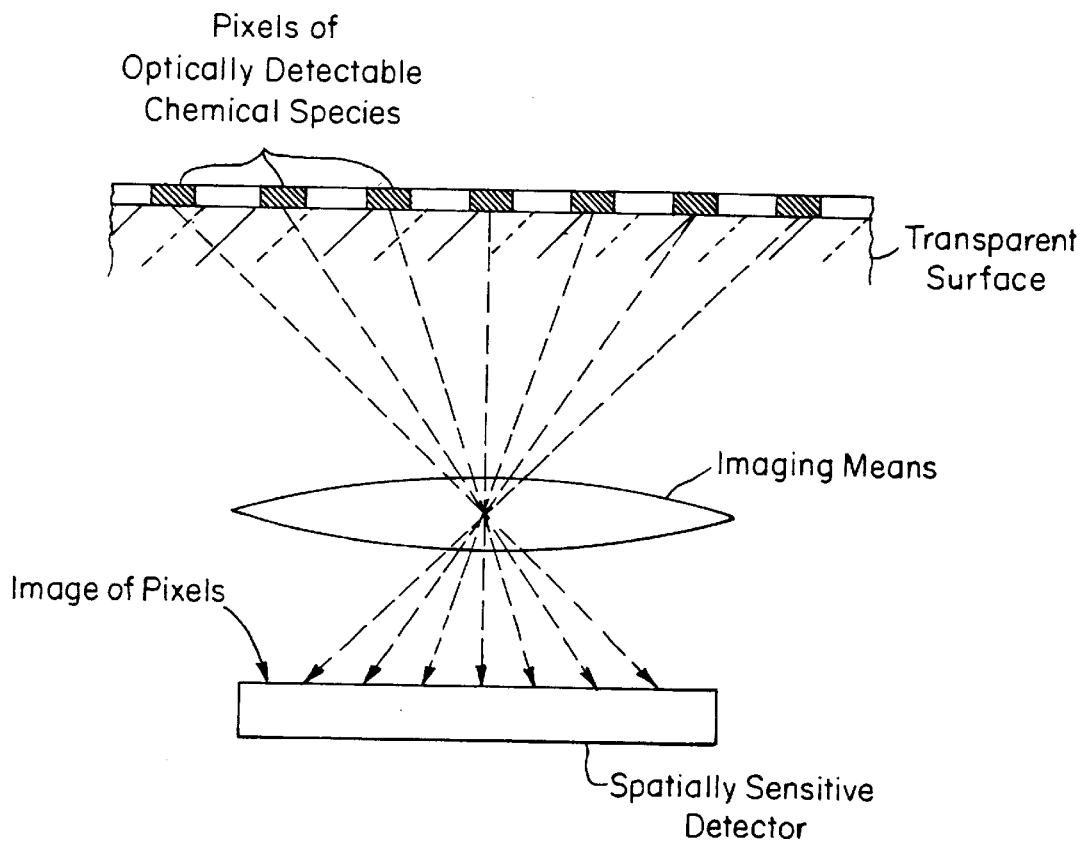

FIG. 6N depicts the case where multiple pixels of attached chemical species are positioned on the surface with a spatial relationship and the detectable signal passes through the transparent surface to a lens or other imaging means that forms an image of the multiple pixels on a spatially sensitive detector able to individually distinguish the imaged pixels such that the presence and image intensity of each pixel can be detected in parallel.

Figure 6O:
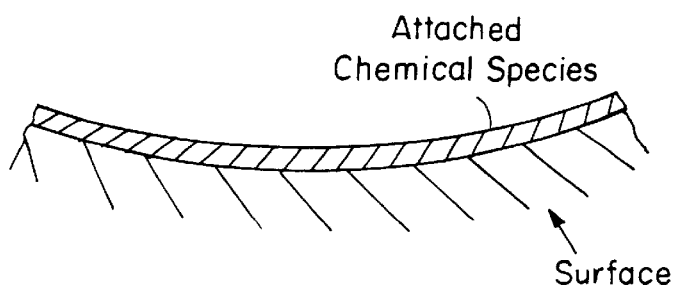

FIG. 6O depicts the case where the surface with attached chemical species is not flat, but is curved in some manner such as cylindrical, spherical, parabaloid or by other mathematical shape or is randomly shaped, and any of the optical excitation and detection configurations herein described are utilized.

Figure 6P:
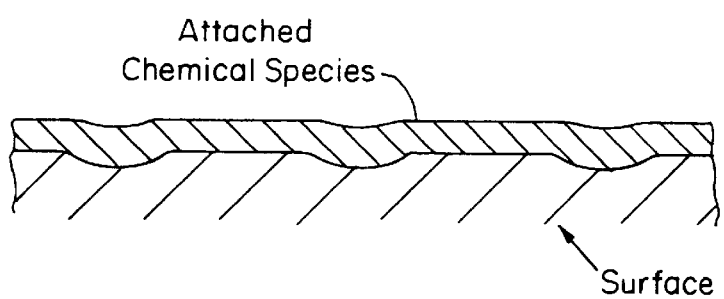

FIG. 6P depicts the case where the surface with attached chemical species is not flat, but has a physical pattern impressed upon it, such as e.g. to positively or negatively indent the surface, such as to provide enhanced locations for concentrating applied sample or chemical species to improve their optical detection by any of the optical excitation and detection configurations herein described.

Figure 6Q:
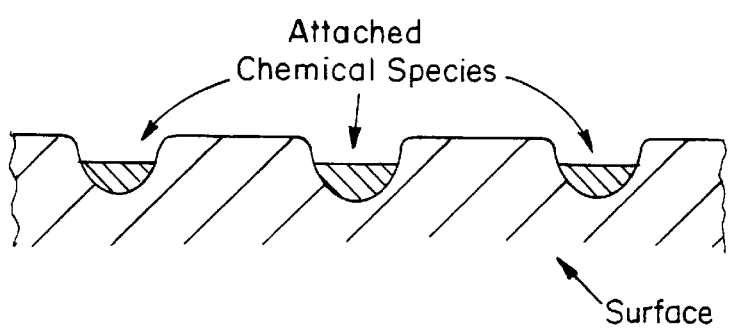
Figure 6R:
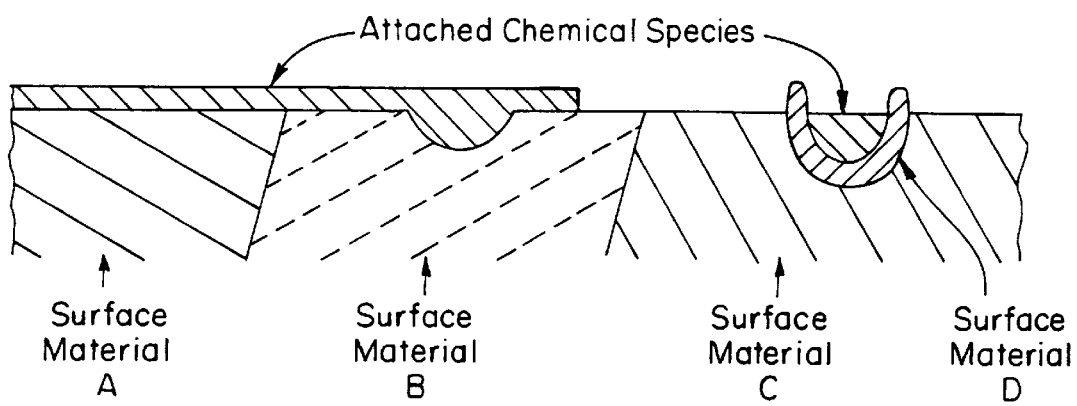

FIG. 6Q depicts the case where the surface with attached chemical species has a pattern impressed upon it such that applied sample or chemical species may be conveniently localized and kept separate and detected by any of the optical excitation and detection configurations herein described.

FIG. 6R depicts the case where the surface with attached chemical species is constructed from two or more separate physical elements which when assembled together topologically represent a single surface of shape as described herein whereon chemical species may be detected by any optical excitation and detection configuration as herein described.

Amplification on an Optical Fiber

Figure 7A:
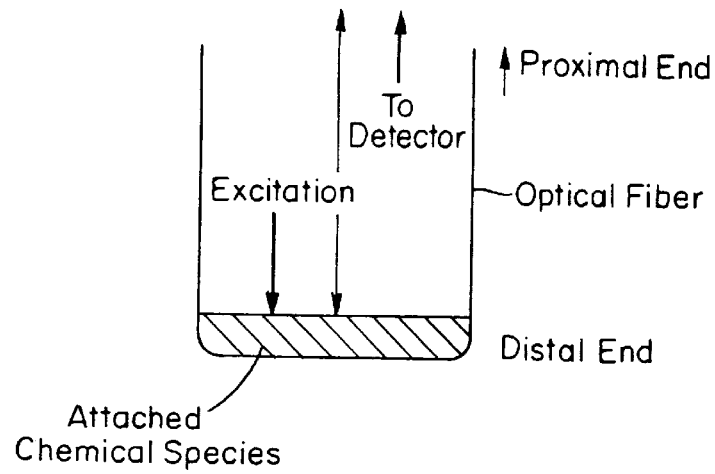
FIGS. 7A–7M depict amplification product detection schemes when the solid support is an optical fiber.

FIG. 7A depicts the case where the optical excitation energy is transmitted from the fiber's proximal end to the distal end to illuminate the attached chemical species on the fiber tip and the detectable signal is transmitted from the distal end to the proximal end where the detector is positioned.

Figure 7B:
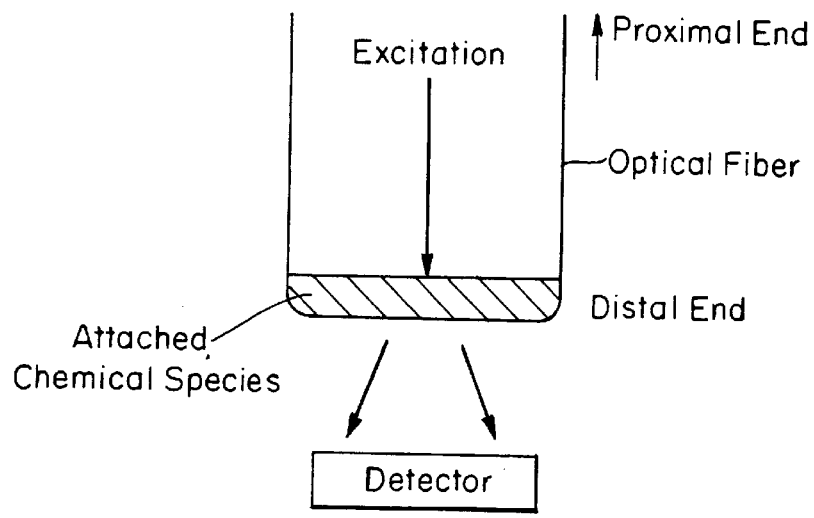

FIG. 7B depicts the case where the optical excitation energy is transmitted from the fiber's proximal end to the distal end to illuminate the attached chemical species on the fiber tip, and the detectable signal is detected from the surface attached chemical species.

Figure 7C:
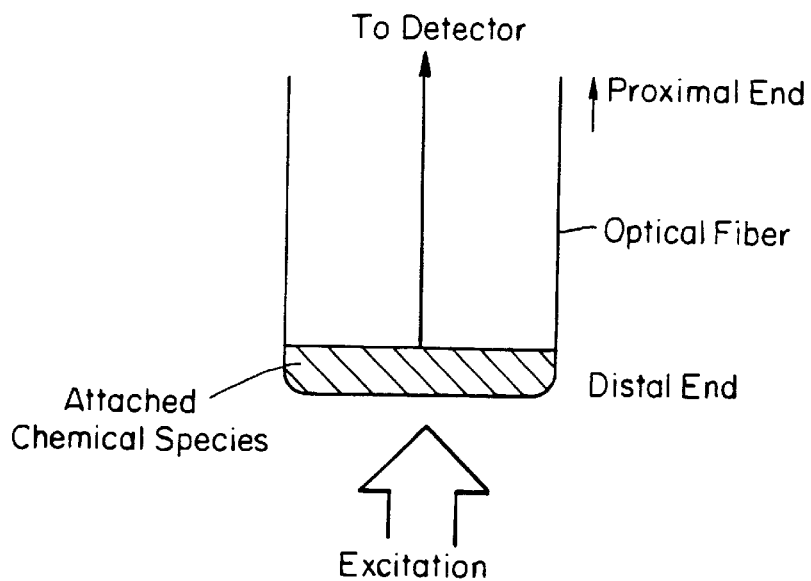

FIG. 7C depicts the case where the optical excitation is directly applied to the attached chemical species on the fiber surface, and the detectable signal is transmitted along the fiber from the distal end to the proximal end where the detector is positioned.

Figure 7D:
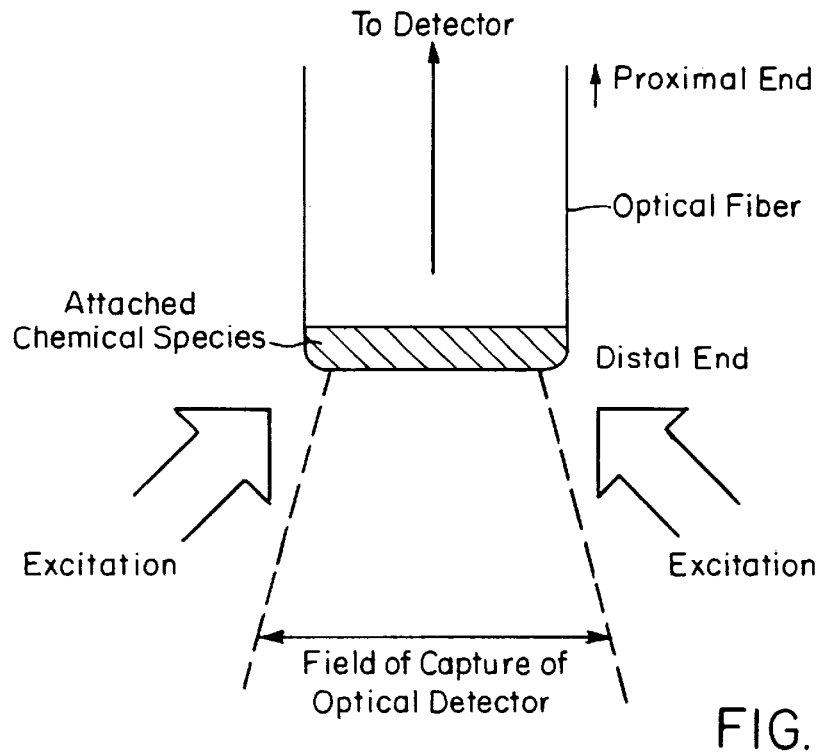

FIG. 7D depicts the case where the optical excitation is directly applied to the attached chemical species on the fiber surface, being limited to such angles as will not be transmitted along the fiber nor therefore captured by the detector, and the detectable signal is transmitted along the fiber from the distal end to the proximal end where the detector is positioned.

Figure 7E:
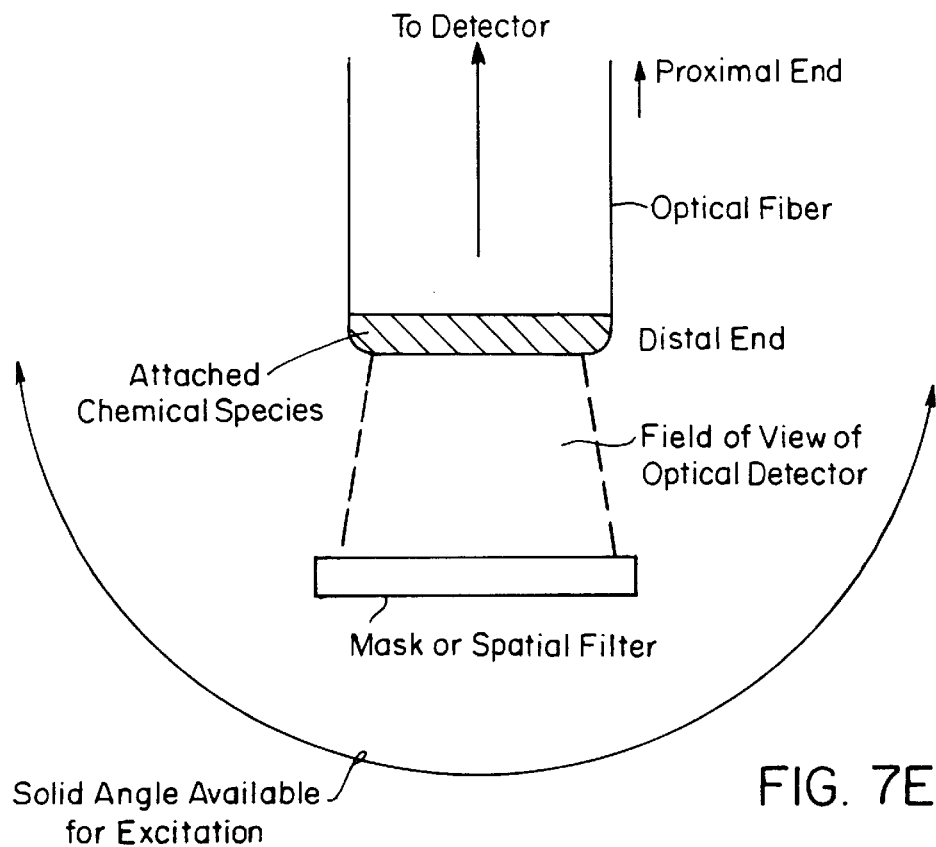

FIG. 7E depicts the case where the optical excitation is directly applied to the attached chemical species on the fiber surface, but with a mask or spatial filter being positioned to prevent excitation from irradiating the distal end from such angles as would be transmitted along the fiber and therefore captured by the detector, and the detectable signal is transmitted along the fiber from the distal end to the proximal end where the detector is positioned.

Figure 7F:
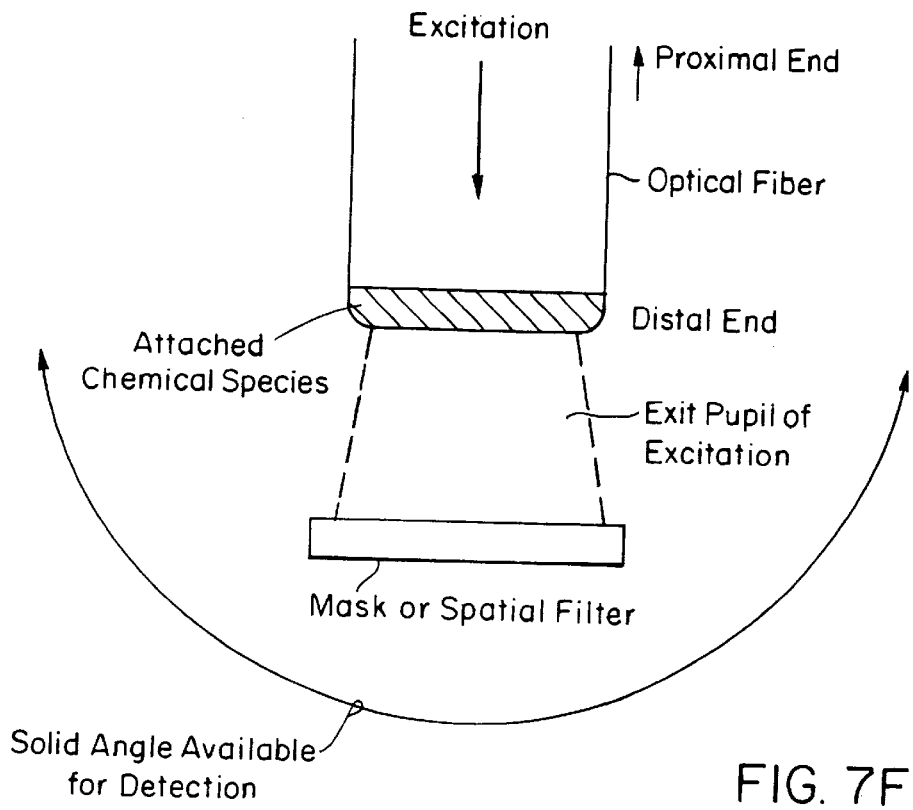

FIG. 7F depicts the case where optical excitation energy is transmitted along the fiber from the proximal end to the distal end to illuminate the attached chemical species on the fiber tip, and the detectable signal is detected from the surface attached chemical species, with a mask or spatial filter positioned to prevent transmitted excitation from the exit pupil of the fiber tip from entering the detector.

Figure 7G:
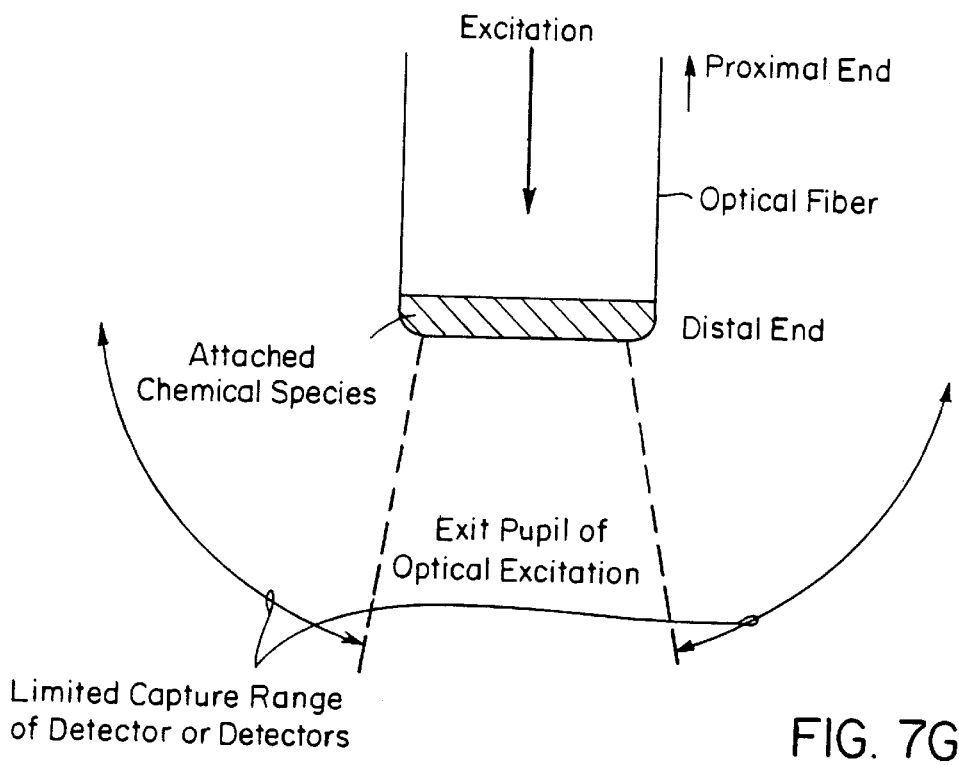

FIG. 7G depicts the case where optical excitation energy is transmitted along the fiber from the proximal end to the distal end to illuminate the attached chemical species on the fiber tip, and the detectable signal is detected from the surface attached chemical species, with the detector or detectors being positioned such as to prevent transmitted excitation from the exit pupil of the fiber tip from entering the detectors.

Figure 7H:
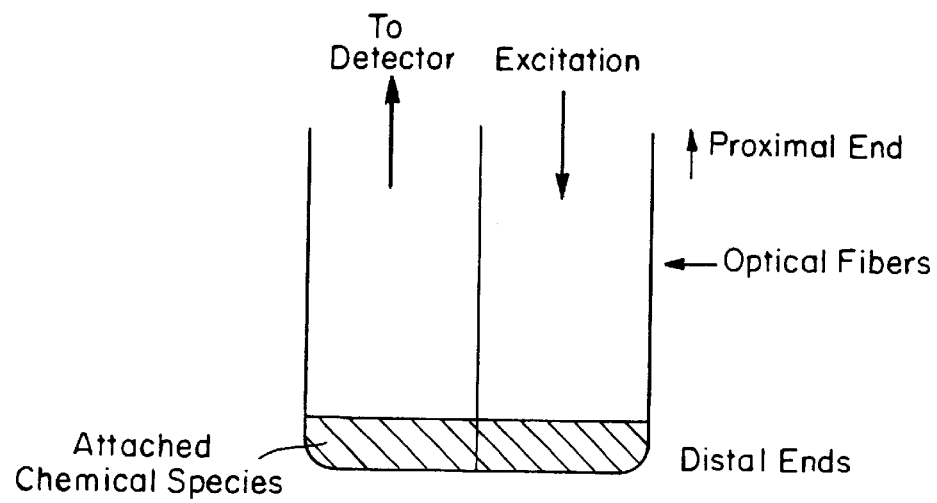

FIG. 7H depicts the case where two or more fibers, individually or within a bundle, are positioned adjacently with attached chemical species positioned at their joint distal end, and optical excitation energy is transmitted from the proximal end to the distal end of one fiber to illuminate the attached chemical species, and the optical signal from the attached chemical species is transmitted from the distal end to the proximal end of the other fiber where it enters a detector.

Figure 7I:
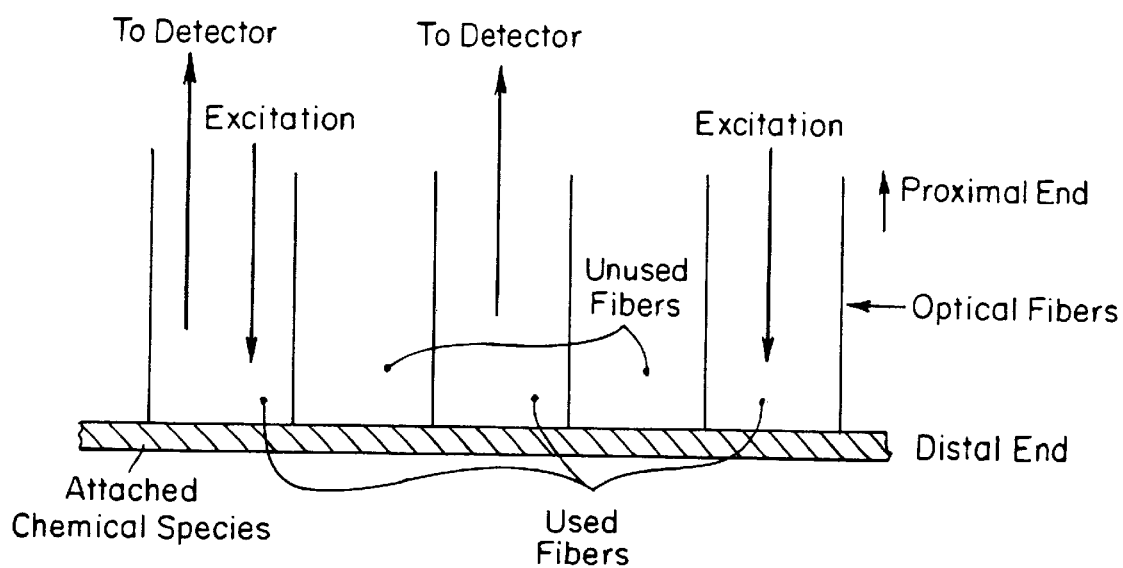

FIG. 7I depicts the case where a fiber is used either to transmit optical excitation energy from the proximal end to the distal end, or to transmit an optical detection signal from the distal end to the proximal end, or to do both, and adjacent fibers individually placed or within a bundle are unused, to prevent optical interference between said fiber and another adjacent fiber similarly used.

Figure 7J:
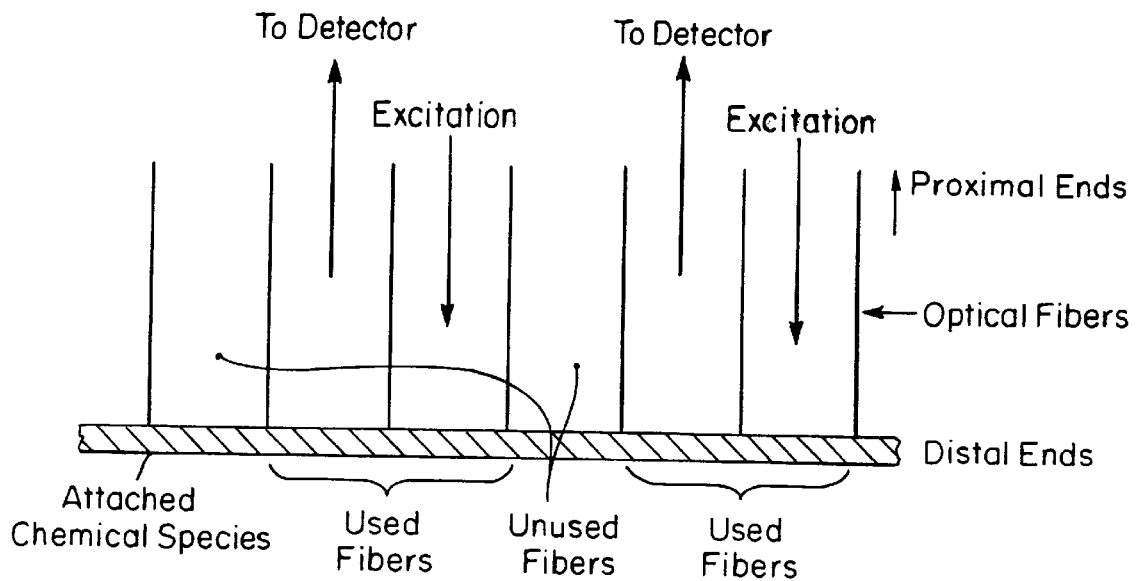

FIG. 7J depicts the case where two or more sets of fibers are placed with at least one unused fiber between adjacent such pair of fibers to prevent optical interference between such sets of fibers, where in each set of fibers one is used to transmit excitation energy from the proximal to the distal end and the other is used to transmit a detection signal from the distal end to the proximal end.

Figure 7K:
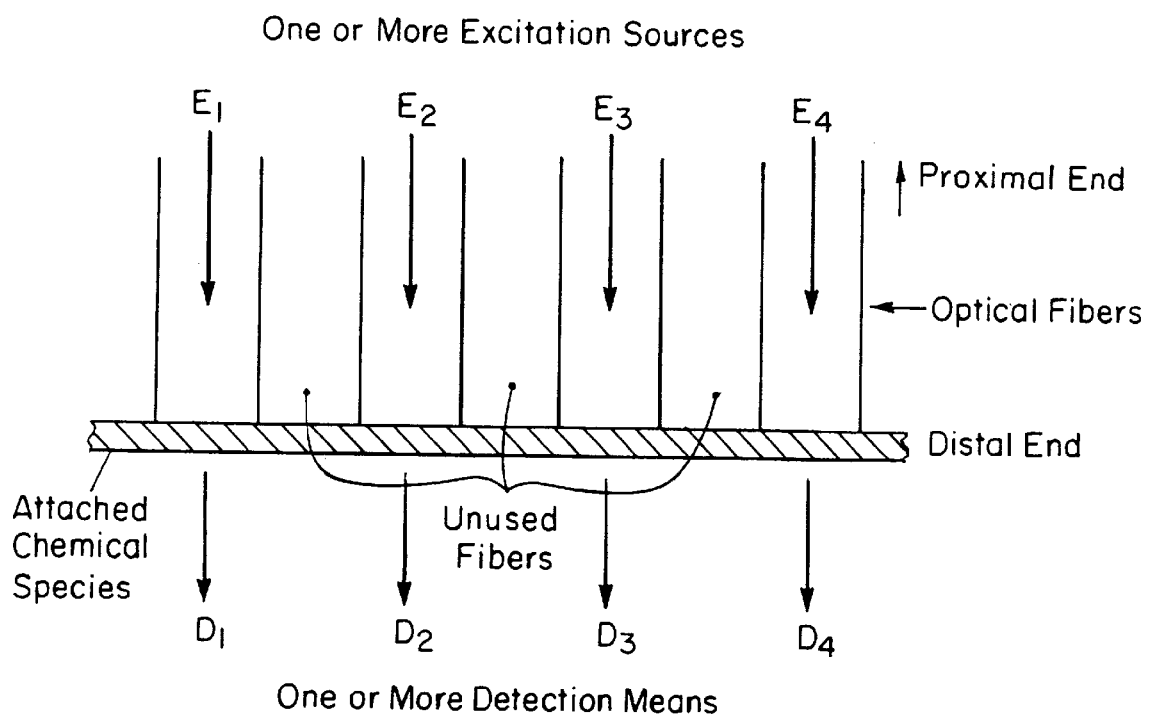

FIG. 7K depicts the case where two or more optical fibers have excitation energy transmitted from their proximal ends to their distal ends to illuminate chemical species attached to the end of each such fiber, and unused fibers are positioned to prevent said fibers from being positioned adjacently and causing optical interference, and the detectable signals from the fibers with chemical species attached are detected by any detection means described herein.

Figure 7L:
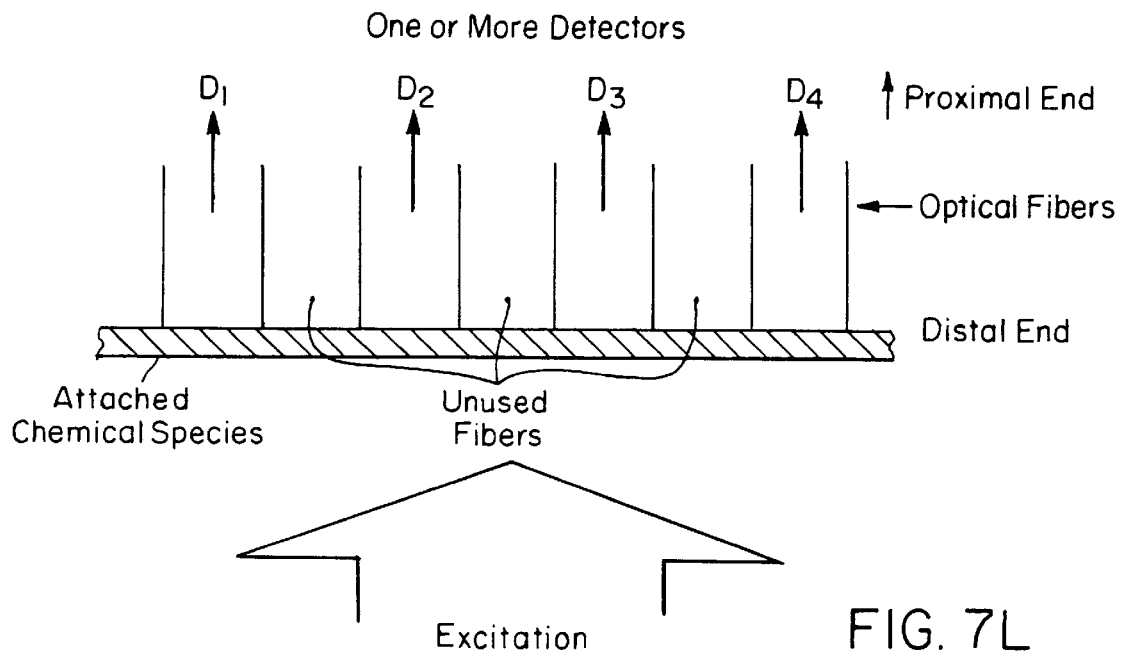

FIG. 7L depicts the case where two or more optical fibers have excitation energy applied to attached chemical species at their distal ends, and detectable signals are transmitted from their distal ends to their proximal ends to one or more detectors, and optionally unused fibers are positioned to prevent said fibers from being positioned adjacently and causing optical interference, and chemical species attached to the end of said fibers are illuminated by any excitation means described herein.

Figure 7M:
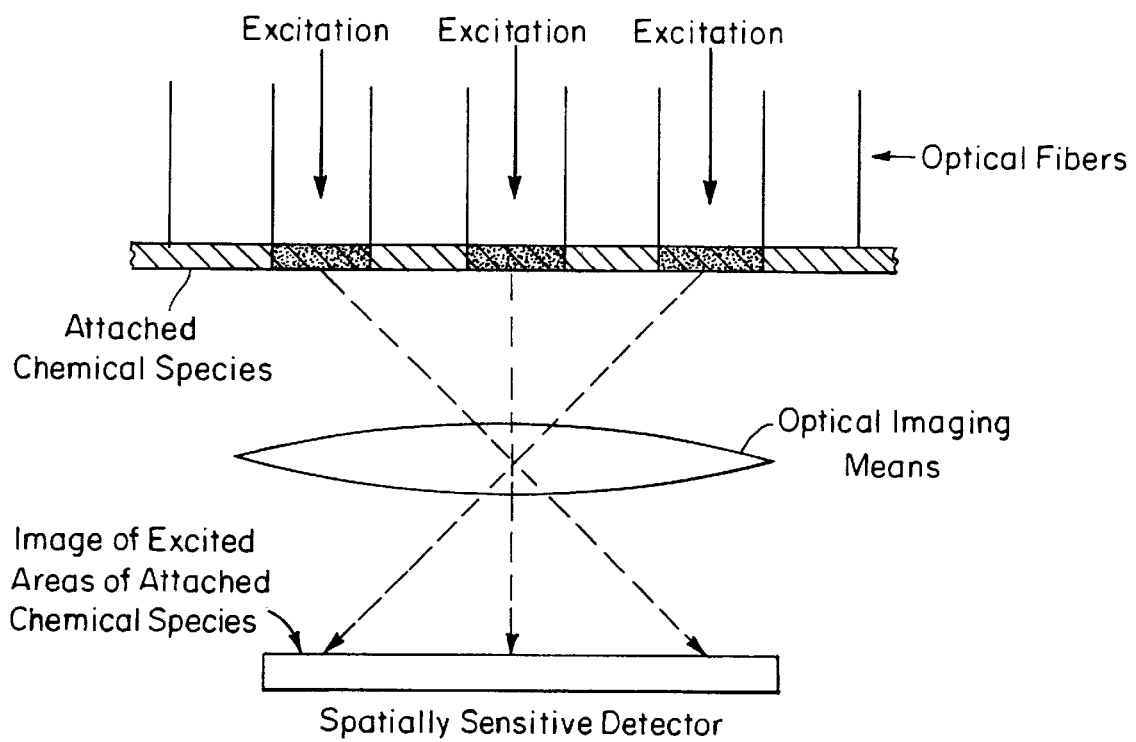

FIG. 7M depicts the case where two or more optical fibers have excitation energy transmitted from their proximal ends to their distal ends to illuminate chemical species attached to the end of each such fiber, and optionally unused fibers are positioned to prevent said fibers from being positioned adjacently and causing optical interference, with the ends of the fibers with detectable chemical species attached being positioned in a spatially significant way, and the detectable signals from said spatially arranged fiber tips with chemical species attached being optically imaged onto a spatially sensitive detector such that all such signals can be detected and optionally quantified simultaneously.

The cases described above are for example only. Other variations are known to those of skill in the optical art. Where direct detection of a detectable signal or application of optical excitation is depicted, this may also be achieved indirectly by known optical relay means including by lenses, mirrors, fiber bundles, filters and beamsplitters, or combinations thereof. Where the chemical species is depicted as simply attached to a surface, this also includes cases where one or more additional layers are positioned above or beneath the attached chemical species, and where the attached layer is shaped, as are herein described. Where optical excitation and detection are explicitly mentioned, this also includes cases where no such optical excitation is required and the detectable signal is induced by other means. Where physical and optical properties only of a surface or fiber tip are depicted, this additionally includes cases where said surface or fiber tip can also be heated or cooled, and its temperature measured, such that this may be temperature controlled, such as for oligonucleotide amplifications by thermocycling.

The following specific examples are provided to illustrate the methods and apparatus contemplated for use in the instant invention. They are not intended to limit the invention in any way.

EXAMPLES

Example 1

Formation of an Elongation Product

This example describes an amplification reaction which results in the formation of an elongation product containing a target nucleic acid sequence. The test sample contains nucleic acid which has been sonicated to produce sequences with an approximate length of 1 kb.

A primer is synthesized with a nucleotide sequence complementary to a region of the target sequence and the primer is immobilized on an epoxy silane derivatized solid support by a 5' amino group. Spacer groups of hexaethyleneglycol are included during synthesis of the primer to eliminate stearic hindrance during the annealing reaction. The spacer region is introduced into the synthesized primer prior to amino group addition, resulting in a calculated spacer region length of 25 angstroms.

The primer is allowed to anneal to the target sequence of the test sample in the presence of thermally stable polymerase, enzyme buffer, $^{32}$P-labeled and unlabeled dNTP to form a reaction mixture. The reaction mixture is heated to 94° C. for one minute for denaturation; cooled to 55° C. for one minute for annealing; and warmed to 75° C. for 5 minutes for extension to form an elongation product extending from the immobilized primer and which is complementary to the target nucleic acid sequence.

This cycle of denaturing, annealing and extension can be performed numerous times, e.g., 30, 50 or more than 100 times, to increase the amount of elongation product to be detected. The reaction mixture is washed from the reaction surface and the immobilized amplification product detected. To eliminate random background noise, the reaction surface is washed using high stringency conditions.

Radiolabeled elongation products are detected using photographic film placed with the emulsion in contact with the solid support. Biotinylated elongation products are detected by analyzing the conversion of a chemiluminescent substrate by a strepavidin-alkaline phosphatase conjugate using x-ray film. Other forms of signal detection can include fluorescence microscopy, fiberoptic devices, confocal microscopy, scintillation detection, piezoelectric material and silicon based systems (i.e., charged coupled devices).

Example 2

Agglutination Assay

This example describes a method of detecting a tartget nucleic acid sequence from HIV. Two oligonucleotide primers of approximately 20 nucleotides in length, and complementary to two different regions of a HIV gene sequence, are immobilized onto a population of derivatized glass beads. One half of the glass beads contain one primer and the other half contains the other primer. In this example, carboxylated derivatized latex particles may be substituted for the derivatized glass beads.

A test sample potentially containing target HIV viral nucleic acid is introduced into a reaction chamber vessel containing the glass beads to form a reaction mixture. The reaction mixture also contains appropriate buffers and enzymes for amplification of target nucleic acid sequence. The reaction mixture is subjected to one or more cycles of denaturing, annealing and extension, thereby amplifying the target nucleic acid.

As amplification of the target sequence proceeds, the primer-coated beads will agglutinate or precipitate. The aggregated or agglutinated complex will be observed spectrophometrically. A decrease in optical density is indicative of the formation of a precipitate and thus the presence of the target nucleic acid. The turbidity of the reaction solution is a function of assay sensitivity and target specificity.

Example 3

Mapping a Target Nucleic Acid Sequence

This example features a protocol for mapping a target nucleic acid, as shown in FIG. 3. A planar derivatized glass support receives pairs of first and second primers. Each primer is approximately 20 nucleotides long. Each pair of primers is complementary to a different sequence corresponding to STS markers along a region of the first nucleic acid. Each set is also positioned in a predetermined area of the glass support and is comprised of approximately 100,000 5' amino linked, second nucleic acids.

A yeast artificial chromosome (YAC) library containing first nucleic acid is divided into pools for screening. The contents of each YAC pool is applied to the support having the second and third nucleic acid primer array along with a reaction mixture of polymerase, buffer, and fluorescein-labeled deoxynucleoside triphosphates. The reaction proceeds for 30 cycles of denaturation, annealing and elongation. Upon completion of the reaction cycles the support is washed to remove unincorporated nucleosides and YACs.

The support is monitored by detecting the presence of amplification products that correspond to a particular YAC pool. Amplification products formed in the presence of a YAC pool in two arrays suggest that the YAC pool contains an adjacent sequence. An amplification product formed by two different YACs, suggest that the two different YACs have an overlapping sequence.

Example 4

Formation of an Amplification Product on Silica Microspheres

This Example highlights the formation of an amplification product on silica microspheres. Rather than forming interlinking beads or microspheres, the amplified product forms a "bridged" product on each sphere analogous to the process of FIG. 2.

As used herein "(4-OmeT)$_8$" indicates an 8 nucleotide stretch containing 4-0-methyl-thymine bases. -5'-NH$_2$-(C6-linker)" indicates that the primers carry a primary amine group linked by a six carbon chain at their 5' ends.

```
Bglo-(-)
5'-NH₂-(C6-linker)-(4-OmeT)₈-GAAGAGCCAAGGACAGGTAC-3'      (Seq. I.D. No. 2)

Bglo-(+)
5'-NH₂-(C6-linker)-(4-OmeT)₈-CCACCTCATCCACGTTCACC-3'      (Seq. I.D. No. 3)

D-13-R
5'-NH₂-(C6-linker)-CTGACCTTAAGTTGTTCTTCAGAAGCAG-3'        (Seq. I.D. No.4)
```

The initial target used for the bridge amplification reaction shown in the example was a 268 base pair double-stranded PCR product that was purified from a solution phase amplification reaction. The solution phase reaction used the Bglo-(+) and Bglo-(-) primers and a human genomic DNA sample. The specific target fragment used in the example was not sequenced, but it can be assumed to be virtually identical to other previously sequenced human beta-globin genes.

The target sequence shown below in Table 1 (Seq. I.D. No. 1) was deduced from GenBank sequence Accession #26462, using the sequence of the Bglo-(+) and Bglo-(-) primers above. The target region overlaps the 5'-end of the coding sequence of the human beta-globin gene. The ATG initiation codon of exon 1 is underlined. The strand with the same sequence as the mRNA is shown.

TABLE 1

5'-GAAGAGCCAA GGACAGGTAC GGCTGTCATC

ACTTAGACCT CACCCTGTGG AGCCACACCC TAGGGTTGGC

CAATCTACTC CCAGGAGCAG GGAGGGCAGG AGCCAGGGCT

TABLE 1-continued

```
GGGCATAAAA GTCAGGGCAG AGCCATCTAT TGCTTACATT

TGCTTCTGAC ACAACTGTGT TCACTAGCCA CCTCAAACAG

ACACCATGGT GCATCTGACT CCTGAGGAGA AGTCTGCCGT

TACTGCCCTG TGGGGCAAGG TGAACGTGGA TGAAGTTG-3'
```

Solid silica microspheres (0.4 micron diameter) were purchased commercially (Bangs Laboratories, Carmel, Ind., USA). A surface epoxide layer was deposited on the microspheres using the method of Chang, Gooding and Regnier, 1976, J. Chromat. 120, 321–333, as described below. A 10% aqueous solution of 3-glycidoxypropyltrimethoxysilane (3-OPTS) was prepared and adjusted to pH 5.7 with 1 millimolar potassium hydroxide, 0.5 milliliters of the 10% 3-OPTS solution were mixed with 100 milligrams of the microspheres suspended in 0.5 milliliters of deionized water. The mixture was held at 88 to 90° C. for 30 minutes. The tube was mixed briefly on a vortex mixer at 5 minute intervals during the incubation. After heating, the beads were washed twice by centrifugation and resuspension in deionized water (1.5 milliliters per wash, 2000 g, 2 minutes).

Epoxide-silica microspheres (50 mg) were washed once in 1.5 milliliters of 0.1 molar potassium hydroxide. The microspheres were centrifuged as described above and resuspended in 75 microliters of 0.1 molar potassium hydroxide containing Bglo-(+) and Bglo-(-) primers each at 29 micromolar concentration. Oligonucleotide D-13-R, 3'-end-labeled with ddATP-alpha-$^{35}$S and terminal transferase, was included at a concentration of 0.2 nanomolar as a tracer to monitor the level of oligonucleotide binding. The derivization was carried out for 8 hours at 37° C., with intermittent vortex mixing to resuspend the microspheres. The microspheres were washed three times by centrifugation and resuspended in 0.1 M potassium hydroxide and twice in deionized water (0.5 milliliters per wash). The microspheres were then resuspended in 200 microliters of 20% ethanolamine (w/v), pH 8.2, and incubated for 8 hours at 37° C. with intermittent mixing. The microspheres were then washed three times by centrifugation and resuspension in an aqueous solution of 0.5% Tween-20 (v/v), 100 micrograms/milliliter bovine serum albumin, (0.5 milliliters/wash). From the level of bound $^{35}$S-labeled-D-13-R primer, the estimated total primer concentration (equimolar (+) and (-) primer) on the microspheres was 2.1–2.2 picomoles per milligram of microspheres.

Primers carrying 5' amino linkers were reacted with the epoxy beads for 12 hours in 0.1 N KOH, at 37° C. The primers used in this experiment amplify a 268 bp target from the human beta-globin gene. Unreacted epoxide groups were eliminated by treating the beads with 2M ethanolamine, pH 8.0, for an additional 12 hours at 37° C.

Using the reasonable assumption that the oligonucleotides bind in a square array on the surface, the spacing between adjacent primers is estimated to be 767 angstroms. This distance is equivalent to the length of a 225 bp fragment of double-stranded DNA.

A 2 mg amount of primer-modified beads was cycled in 100 μl reactions containing: 10 mM Tris HCl (pH 8.3 at 25° C.), 100 μg/ml BSA, 0.5% Tween 20, 5 U Tth polymerase, 200 μM each dNTP, and 0.25 μM dCTP-alpha-$^{32}$P (800 Ci/mmole). The initial target used was 0.45 pmole of the 269 bp beta-globin PCR product, purified from a solution phase PCR reaction by Centricon-100 ultrafiltration. Cycling was carried out for 35 cycles using 1 minute at 94° C., followed by 5 minutes at 60° C.

At each time point, aliquots containing 0.35 mg of beads were removed and washed on 0.2 micron centrifugal filters with 10 mM Tris HCl, pH 7.6, 1 mM EDTA, 0.5% Tween 20. Beadbound radioactivity on the filters was determined by Cerenkov counting. The bound radioactivity cannot be removed by washing at 94° C suggesting that the measured radioactivity is covalently bound to the surface, and not merely adsorbed or hybridized to the primers.

Figure 4:
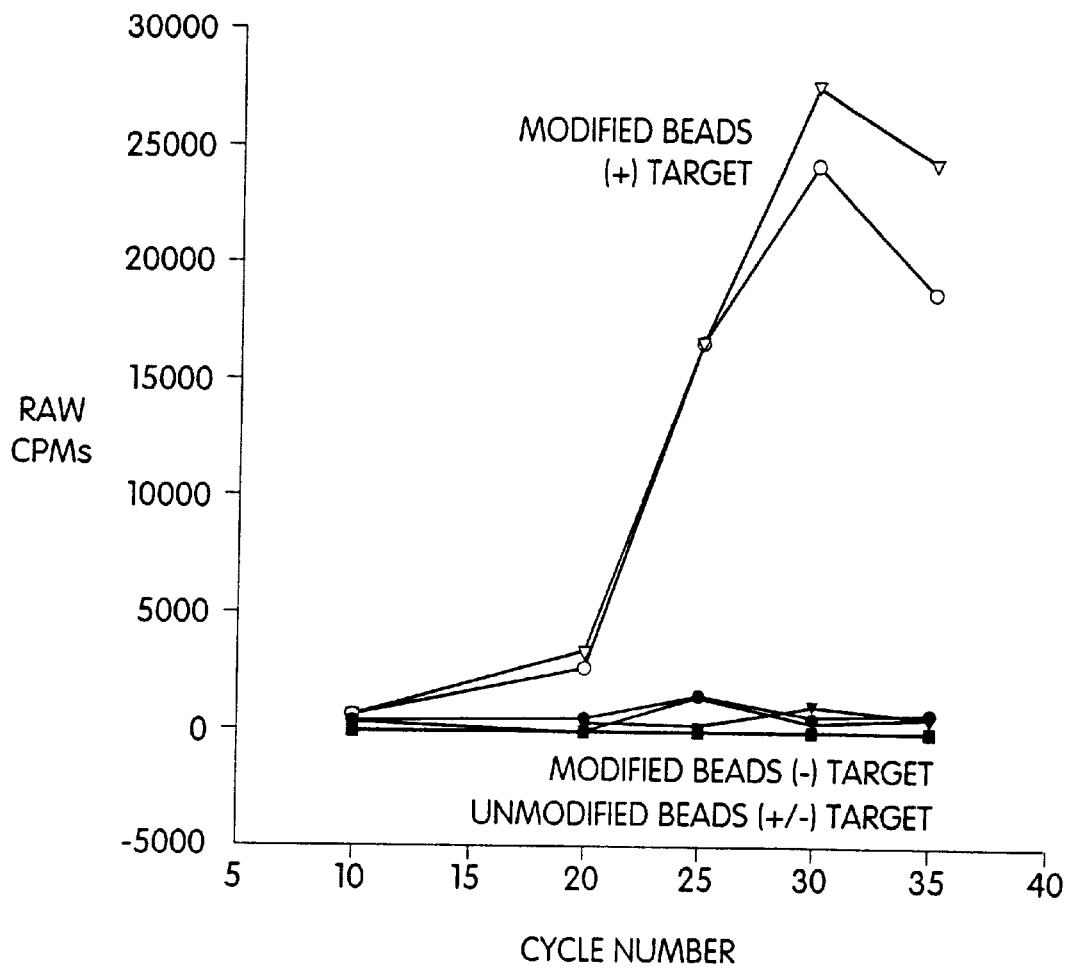
FIG. 4 is a graph depicting the kinetics of the amplification process in accordance with the present invention.

The data demonstrate target-and-primer-dependent incorporation of radioactive DNTP into bead-bound form. These data are described in FIG. 4 as counts per minute. As shown in FIG. 4, open circles and triangles represent reactions of beads carrying the (+) and (-) primers and reactions in the presence of target. Closed circles represent a reaction of beads carrying the (+) and (-) primers in the absence of target. Closed squares represent beads without the (+) and (-) primers in the presence of target, and closed triangles represented beads without the (+) and (-) primers in the absence of target. No incorporation signal is obtained from primer-modified beads in the absence of target (closed circles), or unmodified beads in the presence or absence of target (closed squares and closed triangles respectively).

In the reactions involving beads with the (+) and (-)primer in the presence of target, incorporation increases 6.5 fold for the 5 cycles following cycle 20. This rate is greater than that expected for primer extension using only solution phase target as template, which would be expected to increase by 5-fold at most reasonably indicating that amplification is taking place on the surface of the beads. Assuming an exponential amplification reaction, the increase in incorporation per cycle is approximately 1.4-fold for cycles 21–25.

To verify that the bead-bound product has the predicted bridge structure, primers directed toward a human dystrophin gene fragment were modified to include restriction enzyme sites. The (+) primer contains an XbaI site and the (-) primer contains a ClaI site.

After amplification, two kinds of bead-bound products are expected. Products formed by interaction between solution phase target and primers will generate simple extension products bound only by a single end. These primary extension products can be released by cleavage with a single enzyme, either XbaI or ClaI depending on the primer extended. In contrast, bridge elongation products are bound by both ends, and therefore can only be released by cleavage with both enzymes.

Amplifications were carried out with epoxy-silica beads modified with the dystrophin primers, using the purified 545 bp dystrophin PCR product as target. After 35 cycles, the beads were washed to remove unbound radioactivity, and split into four equal portions. One portion was left in restriction buffer without enzyme, two portions were singly digested with ClaI or XbaI, and one portion was digested simultaneously with both enzymes. After digestion the beads were pelleted by centrifugation, and the supernatants were analyzed by acrylamide gel electrophoresis and autoradiography.

A prominent 545 bp product was clearly visible in the lanes from target-containing reactions, but not in target-(-) controls.

Single enzyme cleavage with either enzyme releases a small amount of primary extension product, and a larger amount is released by double digestion. Densitometric analysis of the bead-bound samples are shown in the lower portion of FIG. 4. The combined integration volume from the two single digests is 1.25 (0.86 "C"+0.39 "X"), while the integration volume from the double digest is approximately 2.7 times greater. These data suggest that 72% of the products found on the beads are in the bridged conformation.

These data indicate that the rate of incorporation is consistent with an exponential process; incorporation increases approximately 1.4-fold per cycle. The predicted specific amplification target is produced in bead-bound form, and most of the bound product is attached in the bridge conformation.

Example 5

DNA Amplification on Optical Fiber Detectors

Fiber optic sensors have been constructed for monitoring hybridization of fluorescently labeled DNA molecules to oligonucleotide probes immobilized on the tip of an optical fiber. Glass optical fiber (0.25 mm diameter) was cleaved and polished according to known procedures. Fiber tips were silanized by soaking in 10% (v/v) aminopropyltriethoxysilane in acetone for 2 hours. The fiber tips were washed in acetone and air dried. The silanized fibers were then soaked in 1.35% glutaraldehyde in 0.02M phosphate buffer (pH 6.8) for 30 minutes. The fiber tips were then rinsed in water and placed in 3% polyethyleneimine (PEI) (2 kd average mol. wt.) in 0.02M phosphate buffer (pH 6.8) for 1–2 hours. The tips of the fibers thus treated were washed in water and 0.1M sodium borate buffer (pH 8.3) (SBB).

A synthetic oligonucleotide designed to recognize human beta-hemoglobin sequences (Bglo probe) was used as a primer. This oligonucleotide primer was obtained commercially with a 5' terminal primary amine group (5'(NH$_2$—(CH$_2$)$_6$—) tt ttt ttt tca act tca tcc acg ttc acc-3', SEQ ID NO:5). The primary amine group was activated with the homobifunctional crosslinking agent, cyanuric chloride, as described by Van Ness et al. (Nucleic Acids Res., 1991, 19:3345–3350).

The hybridization primer was coupled to the PEI-coated fiber by soaking the fiber in a 50–100 μM solution of the activated Bglo probe in SBB for 1–2 hours. Subsequently, unreacted amines were capped by reacting the fiber tips with succinic anhydride (1 hour soak in 0.1 M succinic anhydride, 0.1M sodium borate (pH 8.3), 50% DMSO). Noncovalently bound oligonucleotide was removed following succinylation by several washes with TE Buffer (10 mM Tris-HCl, pH 8.3, 1 mM EDTA).

Primer surface density was not determined directly. However, in analogous experiments using PEI coated microsphere supports, primer densities of 1–10 fmoles primer per mm$^2$ are routinely achieved, as assessed by hybridization with $^{32}$P-labeled complementary oligonucleotides and as described in the previous examples.

The primer-modified end of the fiber was annealed at room temperature by immersing it in a microcentrifuge tube containing labeled oligonucleotide (0.1–1.0 μM) in buffer (TE buffer with 0.2M NaCl and 0.5% SDS) for 15 minutes. Following annealing, the fiber tip was washed by dipping several times in buffer without target oligonucleotide. Fluorescence intensity data were collected using an epifluorescence microscope modified as described in Bronk et al., Anal. Chem. 1995, 67:2750–2757. Briefly, the microscope is modified by replacing the condenser with a fiber holder. The sensor-distal end of the fiber is placed in the holder and imaged using epifluorescence illumination. Fluorescence intensity of the fiber is determined using a microcomputer-controlled CCD camera and image analysis software.

Figure 5:
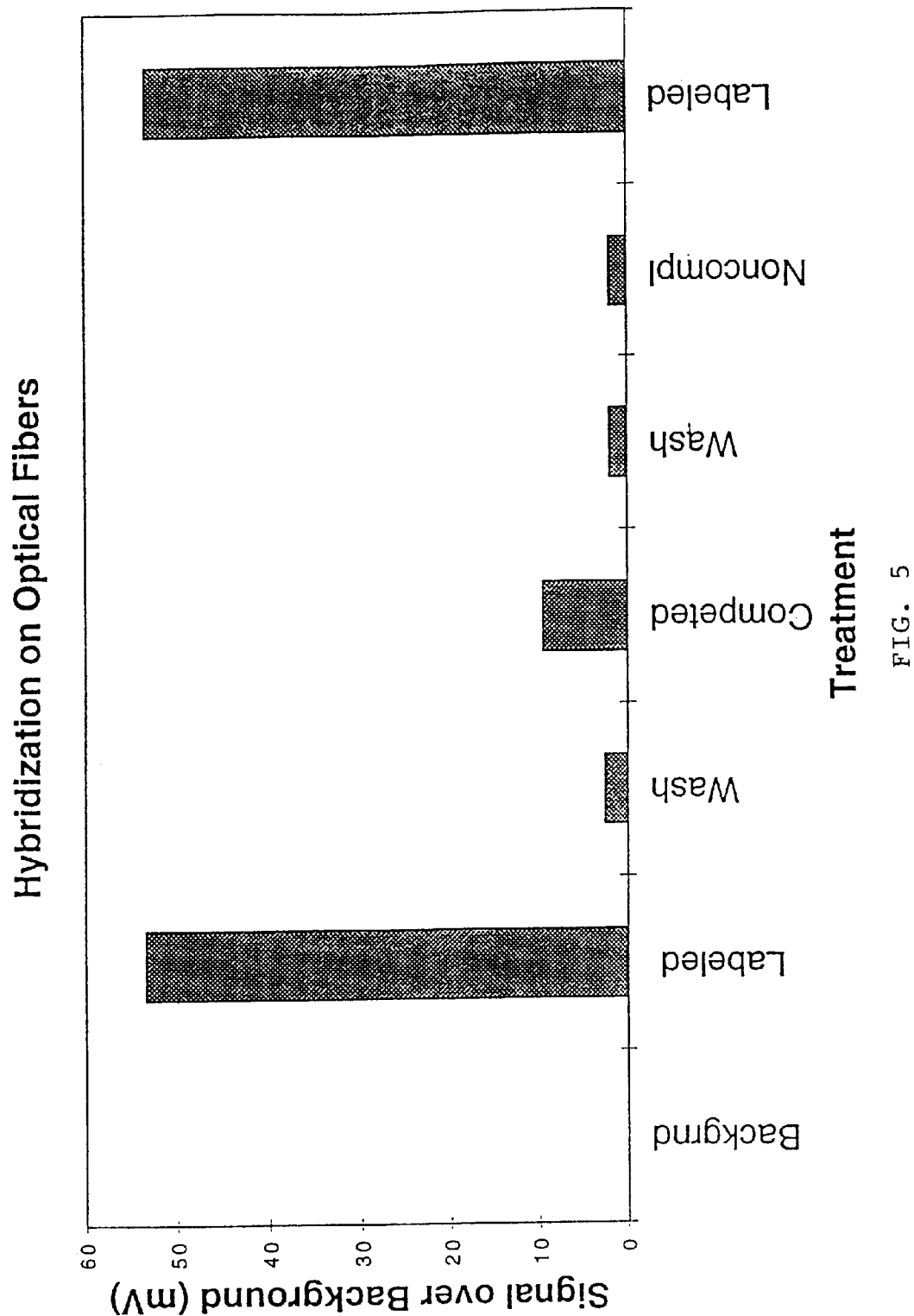
FIG. 5 is a graph illustrating the performance of an optic fiber detector.

The left panel of FIG. 5 illustrates the performance of the sensor. A Bglo-modified fiber was sequentially hybridized to complementary and noncomplementary fluorescein tagged oligonucleotide targets. High hybridization signals were obtained from reactions using a fluorescein-labeled complementary target (Bglo-CF target, 5'-fluorescein-tg aac gtg gat gaa gtt g-3') (SEQ ID NO:6) at concentrations of 0.1 μM and 1.0 μM. The signals were completely eliminated by a denaturing wash in 90% buffered formamide, demonstrating that the signal is completely reversible. No signal was obtained after hybridization to 1.0 μM noncomplementary target (2D-CF target, 5'-Fluorescein-cc cag agg ttc ttt gag tcc tt-3', SEQ ID NO:7), showing that the hybridization signals obtained earlier depend on specific complementary base pairing. High signals were obtained after the fiber was rehybridized to complementary target, showing that the primers were not removed by the formamide wash.

The right-hand panel of FIG. 5 shows a control experiment, where fluorescent beta-globin target was hybridized to an underivatized fiber (no attached primers). Non-specific binding was very low.

Example 6

Bridge Amplification of Target DNA on Optical Fibers

Amplification of target DNA sequences may be detected during, or after the amplification reaction. For end point detection procedures, PEI-coated optical fibers are prepared as described in Example 7 above. Amplification primers carrying 5' terminal amines are covalently attached to the PEI layer using the cyanuric chloride method of Van Ness et al. (Nucleic Acids Res., 1991, 19:3345–3350). For bridge amplification assays, two amplification primers, mixed in a 1:1 molar ratio, are attached to each fiber.

Reactions (50 μl) are carried out using 10 mM Tris-HCl (pH 8.3 at 25° C.), 50 mM KCl, 2.5 mM MgCl$_2$, 200 μM each dNTP, 100 μg/ml BSA, 0.5% Tween 20, 0.05 U/μl AmpliTaq DNA polymerase (Perkin Elmer). To perform the bridge amplification assay, the sample to be tested is added to the reaction mixture and the distal tip of the fiber is immersed in the mixture. The surface of the reaction mixture is overlaid with oil, and the reactions are thermocycled in standard programmable instruments (for instance, Perkin-Elmer 2400). Typical PCR cycling profiles are used: 10 seconds at 94° C. to denature, 10 seconds at temperatures between 50° C. and 72° C. to allow primer annealing (primer sequence-dependent), and 30–60 seconds at 72° C. to allow polymerase extension.

Negative control amplification reactions without added sample are carried out in parallel with the experimental samples to assess the level of target-independent background signal. Positive control reactions are also carried out using known amounts of previously characterized target nucleic acid to ensure that the amplification reagents and instruments are functioning properly.

Following amplification, the fibers bearing the bridge amplification reaction product are removed from the amplification mixture, washed with 10 mM Tris-HCl pH 8.3, 1 mM EDTA, 0.1% Tween 20 (TE/Tw), and the tips are immersed in a solution of 0.1 μM Hoechst 33258 (H33258) in TE/Tw for 5 minutes. H33258 is a DNA stain that fluoresces brightly when bound to double-stranded DNA. Thus, the dye is particularly suitable for use in the present assay as free H33258 dye, or dye bound to single-stranded DNA has a 25-fold lower fluorescence yield (Eggleston et al. 1996, Nucleic Acids Res. 24:1179–1186).

Fluorescence signal is quantified using a fiber optic fluorimeter with capabilities similar to that described by Bronk et al., Anal. Chem. 1995, 67:2750–2757. Elevated H33258 fluorescence signals, defined relative to the values obtained from the negative control reactions, are indicative of the presence of amplified product on the fiber tip. This, in turn, indicates the presence of the nucleic acid target in the original sample.

For detecting amplified product in real time, fiber-based bridge amplification is carried out as described above, except that 0.1 $\mu$M H33258 dye is included in the reaction mixture. H33258 fluorescent signal is measured at the end of each extension cycle. In this way, the progress of the amplification reaction can be followed in a cycle-by-cycle fashion. This capability is particularly useful for quantifying initial target DNA concentrations in experimental samples (Higuchi R, et al. 1993. Bio/technology 11, 1026–1030).

Example 7

Oligonucleotide Ligation Assay on Fiber Optic Supports

In a oligonucleotide ligation assay, two oligonucleotides are designed to hybridize in exact juxtaposition to a target DNA sequence, permitting their covalent joining by DNA ligase. In this embodiment of the invention, a first oligonucleotide is attached to the surface of the fiber as described above in Example 5. The fiber is then immersed in a test sample suspected of containing the target DNA sequence. The test sample further comprises a second detectably labeled oligonucleotide and DNA ligase. The test sample is subjected to conditions that permit hybridization of the first and second oligonucleotides to the target DNA sequence. If the two oligonucleotides hybridize in exact juxtaposition, a suitable substrate for DNA ligase is created. Ligation of the second detectably labeled oligonucleotide to the first oligonucleotide affixed to the optical fiber is then detected via the signal sent through the fiber to the detector at the proximal end.

Example 8

DNA Repair Assays On Optical Fiber Supports

The following example illustrates the use of a fiber optic approach to measure the DNA repair resulting from damage caused by the chemotherapeutic agent, cis-diamminedichloroplatinum (cisplatin).

Two 70 base oligonucleotides are synthesized with complementary base sequences. One is synthesized with a 5' terminal primary amine group to provide a site for attachment to the fiber optic tip. The two oligonucleotides are mixed in an equimolar mixture and hybridized in 10 mM Tris-HCl pH 8.3, 0.2M NaCl, 1 mM EDTA by heating the mixture to 94° C. and cooling to room temperature over a 1 hour period to form a double-stranded 70 bp oligonucleotide. The double-stranded oligonucleotide is purified from unhybridized single stranded oligonucleotides by ion-exchange chromatography.

Following purification, lesions are then introduced into the DNA as follows. The double stranded 70-mer is treated with cisplatin in 10 mM Tris-HCl pH 8.3, 1 mM EDTA (TE buffer) to achieve adduct formation in the range of 1 to 3 cisplatin adducts per oligonucleotide on average. The cisplatin-modified oligonucleotides are then purified by ethanol precipitation from solutions containing 0.5 M NaCl.

The cisplatin-modified oligonucleotides are coupled to PEI-coated optical fibers using the cyanuric chloride method of Van Ness et al. (Nucleic Acids Res. 1991, 19:3345–3350) as generally described in Example 5 above. To provide a negative control value for the assay, a parallel set of fibers are coupled with untreated, adduct-free 70 base pair test duplex oligonucleotide.

To analyze a patient's cisplatin repair capacity, a blood sample is collected and white blood cells are purified. From these cells, a whole-cell lysate is prepared by the method of Manley et al. (Proc. Natl. Acad. Sci. USA, 1980, 77, 3855–3860). Fluorescein-tagged nucleotide triphosphates are added to the lysate (final concentration approximately 500 $\mu$M) and the tips of two fibers, carrying cisplatin-treated and control duplexes, respectively, are immersed in the sample. After incubation for 1 hour at 37° C. to allow repair of the cisplatin adducts and incorporation of fluorescein-labeled nucleotide during repair DNA synthesis, the fibers are removed and washed in TE buffer. A fiber fluorimeter with capabilities similar to that described by Bronk et al. Anal. Chem. 1995, 67:2750–2757, is used to measure the presence of fluorescein-tagged nucleotide on the fiber tips. If the patient is proficient in repair of cisplatin adducts, the fiber with the cisplatin-modified duplex will show a significantly greater fluorescein signal than the fiber with the unmodified control duplex.

In an alternative embodiment, a biopsy sample of a tumor is obtained from a patient. Tumors cells are grown in culture using standard cell culturing techniques known to those of skill in the art. After approximately 10–20 cell divisions, a lysate is prepared as described above. 70-mer oligonucleotides are also prepared as described above. Following purification, a series of the oligomers are treated separately with a variety of known chemotherapeutic agents to induce lesions in the DNA. These agents may include but are not limited to cisplatin, sulfur, nitrogen mustards, enediene compounds, methylating compounds, or the like. Following treatment with chemotherapeutic agents, the oligonucleotides are then purified as described above. The modified oligomers are then coupled to PEI-coated optical fibers using the cyanuric chloride method of Van Ness et al. (Nucleic Acids Res. 1991, 19:3345–3350). To provide a negative control value for the assay, a parallel set of fibers are coupled with untreated, lesion-free 70 base pair test duplex oligonucleotide.

To assess the repair capacity of the tumor lysate, fluorescein-tagged nucleotide triphosphates are added to the lysate (final concentration approximately 500 $\mu$M) and the tips of two fibers, carrying the chemotherapeutic agent-treated and control duplexes, respectively, are immersed in the lysate sample. After incubation for 1 hour at 37° C. to allow repair of the DNA lesions and incorporation of fluorescein-labeled nucleotide during repair DNA synthesis, the fibers are removed and washed in TE buffer. A fiber fluorimeter with capabilities similar to that described by Bronk et al. Anal. Chem. 1995, 67:2750–2757, is used to measure the presence of fluorescein-tagged nucleotide on the fiber tips. If the tumor cells of the patient are proficient in repair of the lesions, the fiber with the chemotherapeutic treated duplex will show a significantly greater fluorescein signal than the fiber with the unmodified control duplex. Optimally, chemotherapeutic agents mentioned above, would be identified that induce lesions in DNA that are inefficiently repaired by the tumor lysate whereas other agents may induce lesions that are readily repaired by the tumor lysate. The above described method facilitates analysis of the repair of lesions induced by the different chemotherapeutic agents and enables an assessment ex vivo of the most efficacious chemotherapeutic agent to employ in treating a patient's cancer.

Example 8

Use of Fiber Optics in a Biosensor System

DNA repair assays on optical fibers may also be used to detect the presence or quantity of unknown DNA damaging agents in aqueous samples from environmental or food sources. In this example, a 70 base pair double stranded oligonucleotide is coupled to the tips of two PEI-coated optical fibers as described in the previous example. One of the fiber tips is immersed in the test sample and incubated to allow damage to occur. The test sample can be an environmental water sample, or aqueous extracts of solid samples such as soil or food. The pH of the sample is controlled in the range of 6–8.5 by addition of appropriate buffers to ensure that the DNA remains in the duplex state and is not depurinated.

Following exposure to the putative carcinogenic sample, the fibers are removed from the sample and washed in TE buffer. The fibers are incubated in a reaction mixture containing bacterial enzymes and cofactors required for excision repair, including the *E.coli* proteins UvrA, UvrB, UvrC, UvrD, DNA polymerase I, DNA ligase, and the cofactors NAD, ATP, and all four deoxynucleoside triphosphates. Additionally, one or more of the deoxynucleoside triphosphates can be fluorescently labeled.

The bacterial Uvr proteins are capable of excising damaged DNA sites caused by a broad spectrum of chemical agents that distort the backbone geometry of the DNA double helix. As a result, if the DNA were damaged by chemicals in the environmental sample, the Uvr proteins will cleave and excise the damaged region. Subsequent resynthesis by DNA polymerase I will incorporate fluorescent nucleotides into the DNA. Fluorescent incorporation is detected using a fiber fluorimeter with capabilities similar to that described by Bronk et al., Anal. Chem. 1995, 67:2750–2757. If damaging agents are present in the sample, the fiber, after contact with the sample, will show much higher fluorescent incorporation than the untreated fiber, thus, confirming the presence of carcinogens in the sample.

Equivalents:

Those skilled in the art will recognize, or be able to ascertain, using no more than routine experimentation, many equivalents to the specific embodiments of the invention described herein.

The invention claimed is:

1. A method of detecting the presence or absence of a target nucleic acid sequence in a test sample comprising the steps of:

a) providing a test sample containing a target nucleic acid sequence;

b) providing an optical fiber having a proximal end and a distal end, said distal end having two or more oligonucleotides immobilized thereon, wherein the nucleotide sequences of the oligonucleotides are complementary to the nucleic acid sequence of the target;

c) contacting the distal end of the fiber with the test sample and maintaining the test sample in contact with the fiber under conditions suitable for the amplification of the target sequence and for time sufficient to obtain a detectable amount of target sequence, thereby producing an amplification product which is immobilized on the optic fiber; and d) detecting the presence of the target sequence in the test sample by the detection of an optically detectable signal produced by the presence of the amplification product.

2. The method of claim 1 wherein amplification of the test sample is by polymerase chain reaction.

3. The method of claim 1 wherein the amplification of the test sample is by ligase chain reaction.

4. The method of claim 1, wherein optical radiation is transmitted along the optical fiber from the proximal end to the distal end where it directly or indirectly irradiates the immobilized amplification product and causes a detectable signal to be generated.

5. The method of claim 1, wherein a signal from the immobilized amplification product is transmitted through the sample and detected.

6. The method of claim 1, wherein the immobilized product is irradiated by optical radiation transmitted along the optical fiber from the proximal end to the distal end, and an optical signal from the product is transmitted through the sample and detected with a dark field optical configuration being used such that said optical radiation does not directly reach the detection means.

7. The method of claim 1, wherein radiation is transmitted through the sample and directly or indirectly irradiates the immobilized amplification product and causes a detectable signal to be generated.

8. The method of claim 1, wherein an optical signal from the immobilized amplification product is transmitted along the optical fiber from the distal end to the proximal end where the optical signal is detected.

9. The method of claim 1, wherein the immobilized amplification product is irradiated by radiation transmitted through the sample, and an optical signal from the product is transmitted along the optical fiber from the distal end to the proximal end and detected with a dark field optical configuration being used such that said optical radiation does not directly reach the detection means.

10. The method of claim 1, wherein optical radiation is transmitted along the optical fiber from the proximal end to the distal end where it directly or indirectly irradiates the immobilized amplification product and causes a detectable signal to be generated, said signal being transmitted along the optical fiber from the distal end to the proximal end where the optical signal is detected.

11. The method of claim 1, wherein in step b) two or more oligonucleotides are immobilized on the optical fiber distal end, wherein the nucleotide sequence of each oligonucleotide is complementary to two or more target nucleic acid sequences in the test sample and two, or more target nucleic acid sequences are detected.

12. The method of claim 11, for determining the presence of two or more target nucleic acid sequences, wherein at least two oligonucleotides are bound to areas of the distal end of a bundle of optical fibers, with each such area being optically distinguishably accessible by one or more optical fibers in said bundle.

13. The method of claim 11, wherein two or more optical fibers are employed whose distal ends adjacently underlie the immobilized amplification product, whereby optical radiation is transmitted along one or more optical fibers from their proximal ends to their distal ends where said radiation directly or indirectly irradiates the surface bound amplification product and causes a detectable signal to be generated, with said signal being transmitted along one or more optical fibers from the distal end to their proximal ends where the optical signal is detected.

14. The method of claim 13, wherein optical radiation is transmitted along two or more optical fibers from their proximal ends to their distal ends where it directly or indirectly irradiates areas of immobilized amplification product and causes one or more detectable signals to be generated, with said signals being detected though the sample.

15. The method of claim 13, wherein optical radiation is transmitted through the sample to directly or indirectly irradiate one or more areas of immobilized amplification product and causes one or more detectable signals to be generated, with said signals being transmitted along one or more optical fibers from their distal end to their proximal ends where the optical signals are detected.

16. The method of claim 1, wherein an optical signal is detected by optical detection means, including optically sensitive diodes, photo multipliers, television cameras, and both linear and two dimensional photosensitive arrays.

17. The method of claim 1, wherein radiation is applied continuously to the amplification product to produce a detectable signal.

18. The method of claim 1, wherein radiation is applied in a time variant manner to the amplification product to produce a detectable signal.

19. The method of claim 1, wherein radiation is applied discontinuously to the amplification product to produce a detectable signal.

20. The method of claim 1, wherein a detectable signal from the amplification product is detected continuously.

21. The method of claim 1, wherein a detectable signal from the amplification product is detected in a time sensitive manner.

22. The method of claim 1, wherein a detectable signal from the amplification product is detected discontinuously.

23. The method of claim 1, wherein the immobilized amplification product is covered by at least one additional layer that has optical filtration properties.

24. The method of claim 1, wherein the immobilized amplification product is underlaid by at least one additional layer that has optical filtration properties.

25. The method of claim 1, wherein the immobilized amplification product is covered by at least one additional layer that has light scattering properties.

26. The method of claim 1, wherein the immobilized amplification product is underlaid by at least one additional layer that has light scattering properties.

27. The method of claim 1, wherein the immobilized amplification product is covered by at least one additional layer that modifies the access of chemical reagents in solution to the distal surface and/or amplified product.

28. The method of claim 1, wherein the immobilized amplification product is covered by at least one additional layer that modifies the rate of formation of amplified product.

29. The method of claim 1, wherein the immobilized amplification product is covered by at least one additional layer that has light reflecting properties.

30. The method of claim 1, wherein the immobilized amplification product is underlaid by at least one additional layer that has light reflecting properties.

31. The method of claim 1, wherein the immobilized amplification product is covered by at least one additional layer that has optical focusing properties.

32. The method of claim 1, wherein the immobilized amplification product is underlaid by at least one additional layer that has optical focusing properties.

33. The method of claim 1, wherein the distal end of the optical fiber is shaped to enhance the signal detection.

34. The method of claim 1, wherein the distal end of the optical fiber is shaped to enhance the irradiation of the amplified product.

35. The method of claim 1, wherein the oligonucleotide of step b) is between about 5 and 100 nucleotides in length.

36. The method of claim 1, wherein the oligonucleotide of step b) is covalently attached to said optical fiber.

37. A method of detecting the presence or absence of a target nucleic acid sequence in a test sample, comprising the steps of:
   a) providing a test sample containing a target nucleic acid sequence;
   b) providing an optical fiber having a proximal end and a distal end, said distal end having two or more oligonucleotides immobilized thereon, wherein the nucleotide sequences of the oligonucleotides are complementary to a sequence flanking the target sequence;
   c) contacting the distal end of said optical fiber with the test sample in the presence of deoxyribonucleotide triphosphates and one or more appropriate enzymes, under conditions suitable for extension of the primer sequence and amplification of the target sequence thereby producing an amplification product; and
   d) detecting the presence of the amplification product, wherein detection of the amplification product is indicative of the presence of the target nucleic acid sequence.

38. The method of claim 37 wherein in step c) the deoxyribonucleotides are detectably labeled and the amplification product is detected by the presence of detectably labeled deoxyribonucleotide in the amplification product.

39. The method of claim 38 wherein the label is an agent selected from the group consisting of chemiluminescent, electrochemiluminescent, luminescent, radioactive, photoabsorbing and fluorescent agents.

40. The method of claim 37 wherein in step c) a detectably labeled moiety which binds to or hybridizes with the amplification product is added optionally either before or during amplification of the target sequence or substantially immediately thereafter completion of amplification and the amplification product is detected by the presence of the detectably labeled moiety bound to or hybridized with the amplification product.

41. The method of claim 40 wherein the label is an agent selected from the group consisting of chemeluminescent, electrochemiluminescent, luminescent, radioactive, photoabsorbing and fluorescent agents.

42. The method of claim 40 wherein the moiety is selected from the group consisting of fluorescent dyes, intercalating agents, nucleic acid probes, nucleic acid analogs, nucleic acid binding proteins, antibodies and chelating agents.

43. The method of claim 37, wherein the primer of step b) is between about 5 and 100 nucleotides in length.

44. The method of claim 37, wherein the primer of step b) is covalently attached to the optical fiber.

45. A method of detecting a target nucleic acid sequence in a test sample, comprising the steps of:
   a) providing a test sample containing a target nucleic acid sequence;
   b) providing an optical fiber having a proximal end and a distal end, said distal end having a first oligonucleotide immobilized thereon, said nucleotide sequence of the oligonucleotide being complementary to a sequence within the target sequence;
   c) contacting the distal end of the optical fiber with the test sample in the presence of a second oligonucleotide being complementary to a sequence within the target sequence that is immediately contiguous with the sequence complementary to the first oligonucleotide sequence and at least one ligase enzyme under conditions suitable for annealing of the first and second oligonucleotides to the target sequence, ligation of the annealed oligonucleotides and amplification of the target sequence, thereby producing an amplification product; and
   d) detecting the presence of the amplification product, wherein detection of the amplification product is indicative of the presence of the target sequence.

46. The method of claim 45 wherein the second oligonucleotide of step c) is detectably labeled and the amplification product is detected by the presence of the detectably labeled second oligonucleotide in the product.

47. The method of claim 46 wherein the label is an agent selected from the group consisting of chemeluminescent, electrochemiluminescent, luminescent, radioactive, photoabsorbing and fluorescent agents.

48. The method of claim 45 wherein in step c) a detectably labeled moiety which binds to or hybridizes with the amplification product is added optionally either during amplification of the target sequence or substantially immediately thereafter completion of amplification and the amplification product is detected by the presence of the detectably labeled moiety bound to or hybridized with the amplification product.

49. The method of claim 48 wherein the label is an agent selected from the group consisting of chemeluminescent, electrochemiluminescent, luminescent, radioactive, photoabsorbing and fluorescent agents.

50. The method of claim 48 wherein the moiety is selected from the group consisting of fluorescent dyes, intercalating agents, nucleic acids probes, nucleic acid analogs, nucleic acid binding proteins, antibodies and chelating agents.

51. A method for determining polynucleotide damage and repair ex vivo in a double stranded oligonucleotide having about 30–500 base pairs and including a lesion, said method comprising:
   a) providing an optical fiber having a proximal end and a distal end, said distal end having a double stranded oligonucleotide immobilized on an optical fiber;
   b) treating said optical fiber having said oligonucleotide immobilized thereto with a composition comprising,
      i. a lysate from a candidate cell population and
      ii. a polynucleotide repair reagent, for a time sufficient for said lysate to act upon said lesion and effect incorporation of said polynucleotide repair reagent into said lesion; and
   c) measuring a property of the oligonucleotide treated as in step b) while coupled to said optical fiber, the resulting measurement being determinative of the extent of repair of said oligonucleotide.

52. A method according to claim 51, wherein said measurement is performed using an antibody specific for polynucleotide lesions, said polynucleotide repair reagent consisting of unlabeled deoxyribonucleotide triphosphates and polynucleotide repair is measured by a loss of antibody binding to said oligonucleotide.

53. A method according to claim 51, wherein said measurement is assessed by determining the amount of signal producing polynucleotide repair reagent incorporated into said polynucleotide, said signal producing polynucleotide repair reagent being selected from the group consisting of radiolabeled deoxyribonucleotide triphosphates, fluoresceinated deoxyribonucleotide triphosphates, and biotinylated deoxyribonucleotide triphosphates.

54. A method for determining the ability of neoplastic cells to repair lesions formed by therapeutic agents in double stranded oligomeric polynucleotide having about 30–500 base pairs, said method comprising:
- a) providing said double stranded oligonucleotide covalently coupled to an optical fiber;
- b) treating said optical fiber having said oligonucleotide covalently coupled thereto with a composition comprising,
  - i. a lysate from said neoplastic cells and
  - ii a polynucleotide repair reagent, for a time sufficient for said lysate to act upon said lesion and effect incorporation of said polynucleotide repair reagent into said lesion; and
- c) measuring a property of the oligonucleotide treated as in step b) while coupled to said optical fiber, the resulting measurement being determinative of the extent of repair of said oligonucleotide.

55. A method according to claim 54, wherein said measurement is performed using an antibody specific for polynucleotide lesions, said polynucleotide repair reagent consists of unlabeled deoxyribonucleotide triphosphates and polynucleotide repair is measured by a loss of antibody binding to said oligonucleotide.

56. A method according to claim 54, wherein said measurement is assessed by determining the amount of signal producing polynucleotide repair reagent incorporated into said polynucleotide, said signal producing polynucleotide repair reagent being selected from the group consisting of radiolabeled deoxyribonucleotide triphosphates, fluoresceinated deoxyribonucleotide triphosphates, and biotinylated deoxyribonucleotide triphosphates.

57. A method according to claim 54, wherein said lesions are the result of radiation.

58. A method according to claim 54, wherein said lesions are the result of exposure to chemotherapeutic agents.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 268 base pairs
      (B) TYPE: nucleic acid
      (C) STRANDEDNESS: double
      (D) TOPOLOGY: linear (xi) SEQUENCE DESCRIPTION: SEQ ID NO:1:

```
GAAGAGCCAA GGACAGGTAC GGCTGTCATC ACTTAGACCT CACCCTGTGG AGCCACACCC      60

TAGGGTTGGC CAATCTACTC CCAGGAGCAG GGAGGGCAGG AGCCAGGGCT GGGCATAAAA     120

GTCAGGGCAG AGCCATCTAT TGCTTACATT TGCTTCTGAC ACAACTGTGT TCACTAGCCA     180

CCTCAAACAG ACACCATGGT GCATCTGACT CCTGAGGAGA AGTCTGCCGT TACTGCCCTG     240

TGGGGCAAGG TGAACGTGGA TGAAGTTG                                        268
```

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:2:

```
GAAGAGCCAA GGACAGGTAC                                                  20
```

(2) INFORMATION FOR SEQ ID NO:3:

(i) SEQUENCE CHARACTERISTICS:
      (A) LENGTH: 20 base pairs

-continued

```
        (B) TYPE: nucleic acid
        (C) STRANDEDNESS: single
        (D) TOPOLOGY: linear (xi) SEQUENCE DESCRIPTION: SEQ ID NO:3:

CCACCTCATC CACGTTCACC                                               20

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:4:

CTGACCTTAA GTTGTTCTTC AGAAGCAG                                      28

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

TTTTTTTTTC AACTTCATCC ACGTTCACC                                     29

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

TGAACGTGGA TGAAGTTG                                                 18

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

CCCAGAGGTT CTTTGAGTCC TT                                            22
```